(12) United States Patent
Chugh

(10) Patent No.: US 10,624,914 B2
(45) Date of Patent: Apr. 21, 2020

(54) METHODS FOR DETERMINING THE LEVEL OF HYPOSIALYLATION OF ANGPTL4

(71) Applicant: Sumant S Chugh, River Forest, IL (US)

(72) Inventor: Sumant S Chugh, River Forest, IL (US)

( * ) Notice: Subject to any disclaimer, the term of this patent is extended or adjusted under 35 U.S.C. 154(b) by 56 days.

(21) Appl. No.: 15/803,524

(22) Filed: Nov. 3, 2017

(65) Prior Publication Data

US 2018/0055865 A1    Mar. 1, 2018

Related U.S. Application Data

(60) Division of application No. 14/943,167, filed on Nov. 17, 2015, now Pat. No. 9,827,259, which is a continuation of application No. 13/152,169, filed on Jun. 2, 2011, now abandoned.

(60) Provisional application No. 61/351,865, filed on Jun. 5, 2010.

(51) Int. Cl.
| | |
|---|---|
| *A23J 1/00* | (2006.01) |
| *C07K 1/00* | (2006.01) |
| *C07K 14/00* | (2006.01) |
| *C07K 17/00* | (2006.01) |
| *C07K 16/00* | (2006.01) |
| *G01N 33/53* | (2006.01) |
| *A61K 31/7008* | (2006.01) |
| *A61K 31/7012* | (2006.01) |
| *C07K 14/435* | (2006.01) |

(52) U.S. Cl.
CPC ...... *A61K 31/7008* (2013.01); *A61K 31/7012* (2013.01); *C07K 14/00* (2013.01); *C07K 14/435* (2013.01); *G01N 2800/042* (2013.01); *G01N 2800/347* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | |
|---|---|---|
| 6,274,568 B1 | 8/2001 | Schnaar et al. |
| 2003/0054517 A1 | 3/2003 | Baker et al. |
| 2005/0054570 A1 | 3/2005 | Rosen et al. |
| 2010/0121040 A1 | 5/2010 | Nakazawa |
| 2010/0249047 A1 | 9/2010 | Huizing et al. |
| 2012/0264928 A1 | 10/2012 | Noguchi et al. |

FOREIGN PATENT DOCUMENTS

| | | |
|---|---|---|
| CN | 101600438 | 12/2009 |
| WO | 2007124750 | 11/2007 |
| WO | 2008150477 | 12/2008 |
| WO | 2009020641 | 2/2009 |
| WO | 2010131712 | 11/2010 |
| WO | 2011153525 | 12/2011 |

OTHER PUBLICATIONS

Galeano et al., J. Clin. Invest. 117:1585-1594 (2007) (Year: 2007).*
Wei et al., Nephrol. Dial. Transplant. 26:1776-1777 (2011) (Year: 2011).*
"Notice of Rejection—Japanese patent application No. 2016-503307" Japanese patent office; date Mar. 27, 2018; pp. 1-4.
Lee Su Jeong "Notice of Decision of Final Rejection—Korean patent application No. 10-2013-7000446" Korean Intellectual Property Office; dated Mar. 13, 2018; pp. 1-3.
Rishu Bharti "Examination Report—India patent application No. 5/DELNP/2013" dated Mar. 21, 2018; pp.
Malicadan, et al. "Prophylactic treatment with sialic acid metabolites precludes the development of the myopathic phenotype in the DMRV-hIBM mouse model" Nature Medicine; vol. 15, No. 6; Jun. 2009; pp. 690-715.
Quaggin, Susan E. "Sizing up sialic acid in glomerular disease" The Journal of Clinical Investigation, vol. 117, No. 6, Jun. 2007, pp. 1480-1483.
Clement Lionel C, et al. "Podocyte-secreted angiopoietin-like-4 mediates proteinuria in glucocorticoid-sensitive nephrotic syndrome" Nature Medicine; vol. 17: No. 1, Jan. 2011; pp. 117-123.
Albayrak, Timur "Supplementary European Search report appln. No. 11790460.7" Nov. 12, 2013; pp. 1-7.
Zhu, et al., Biosci. Rep., 2012, 32, p. 211-219.
Definition of precursor, Oxford English Dictionary, http://www.oed.com/view/Entry/149764?redirectedFrom=precursor&print, accessed online on Apr. 28, 2017.

* cited by examiner

*Primary Examiner* — James H Alstrum-Acevedo
*Assistant Examiner* — Thea D'Ambrosio
(74) *Attorney, Agent, or Firm* — Thomas G. Peterson; Maynard Cooper & Gales

(57) ABSTRACT

The present disclosure provides a biochemical basis of nephrotic syndrome and provides and explanation for the observed proteinuria and other effects. As a result, the present disclosure provides method for treating and/or preventing nephrotic syndrome as well as methods of alleviating symptoms associated with nephrotic syndrome. The present disclosure further provides methods for reducing proteinuria in nephrotic syndrome and other disease states as discussed herein.

8 Claims, 10 Drawing Sheets

Specification includes a Sequence Listing.

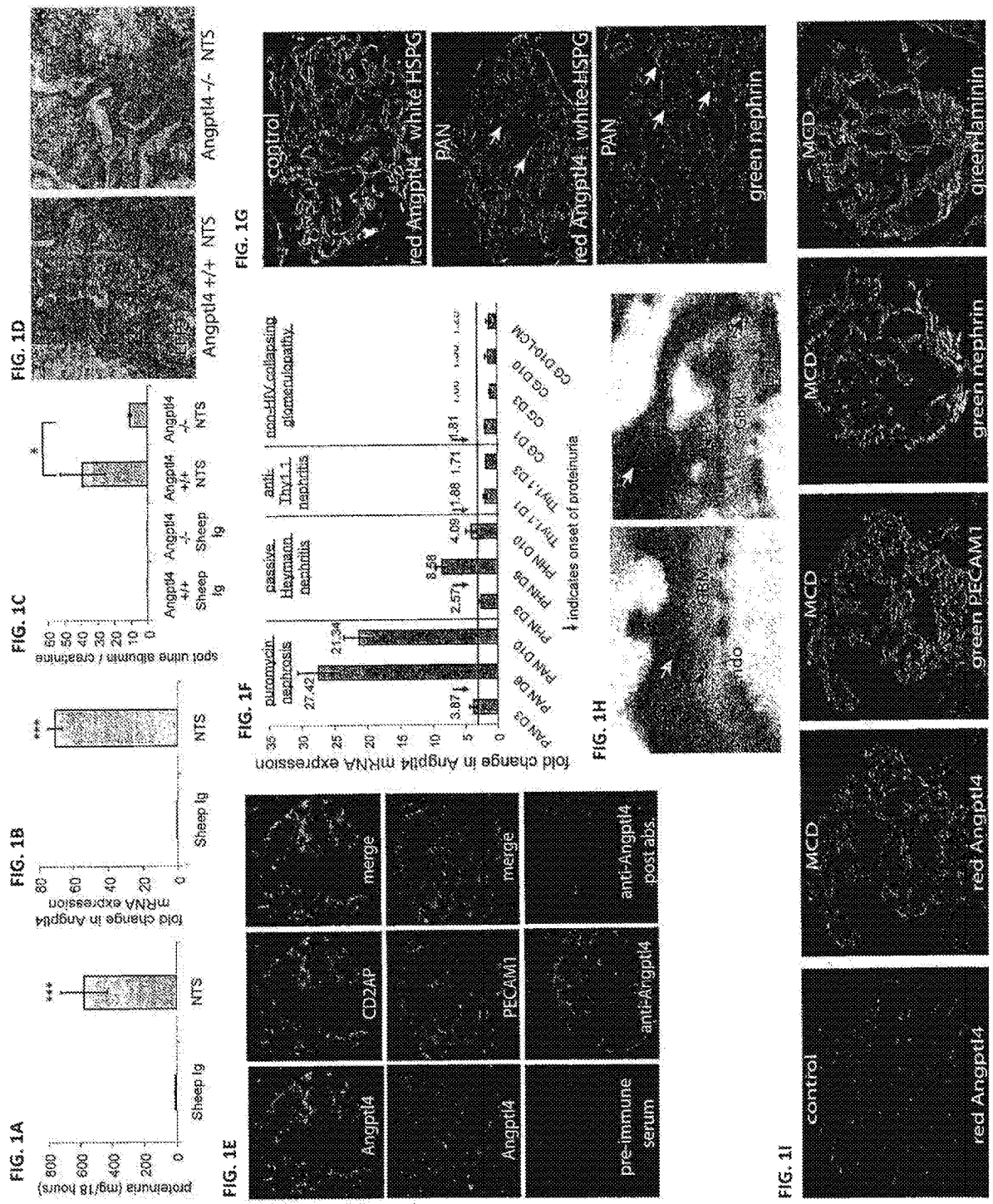

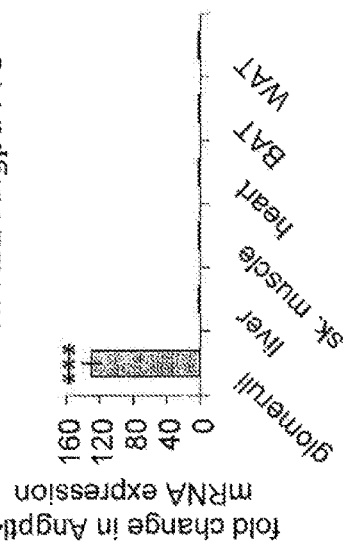
FIG. 2A
FIG. 2B
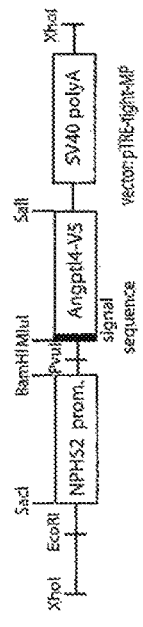
FIG. 2C
FIG. 2D
FIG. 2E
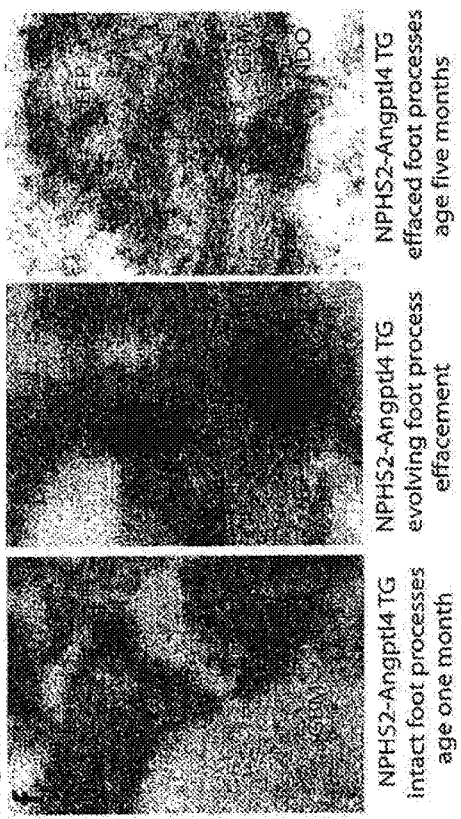
FIG. 2F
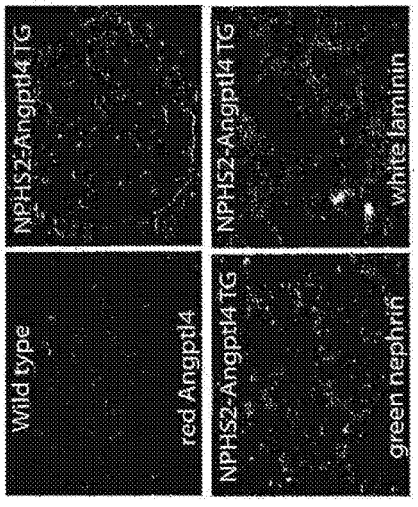

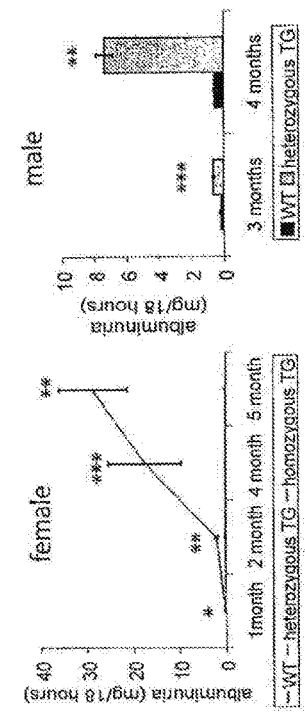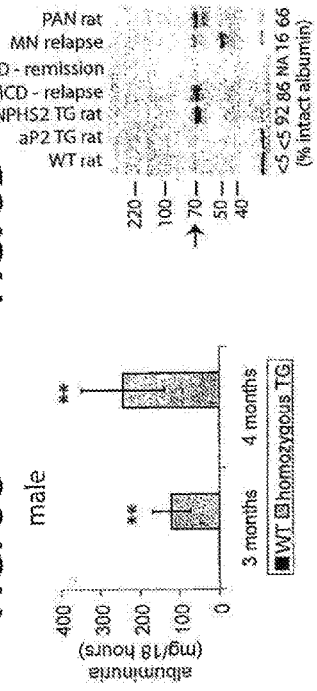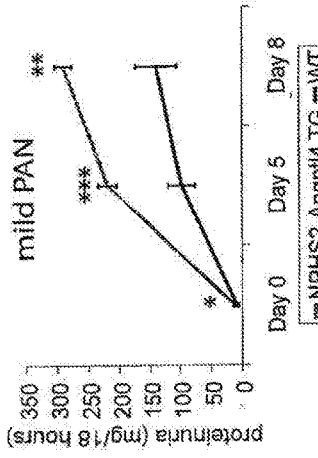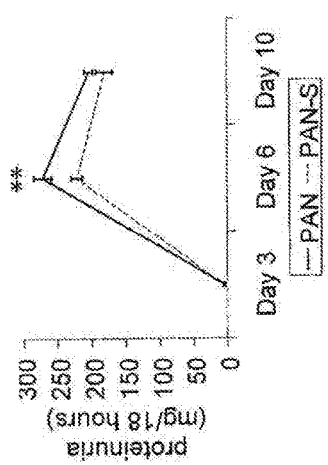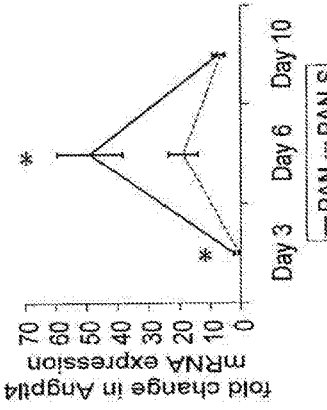

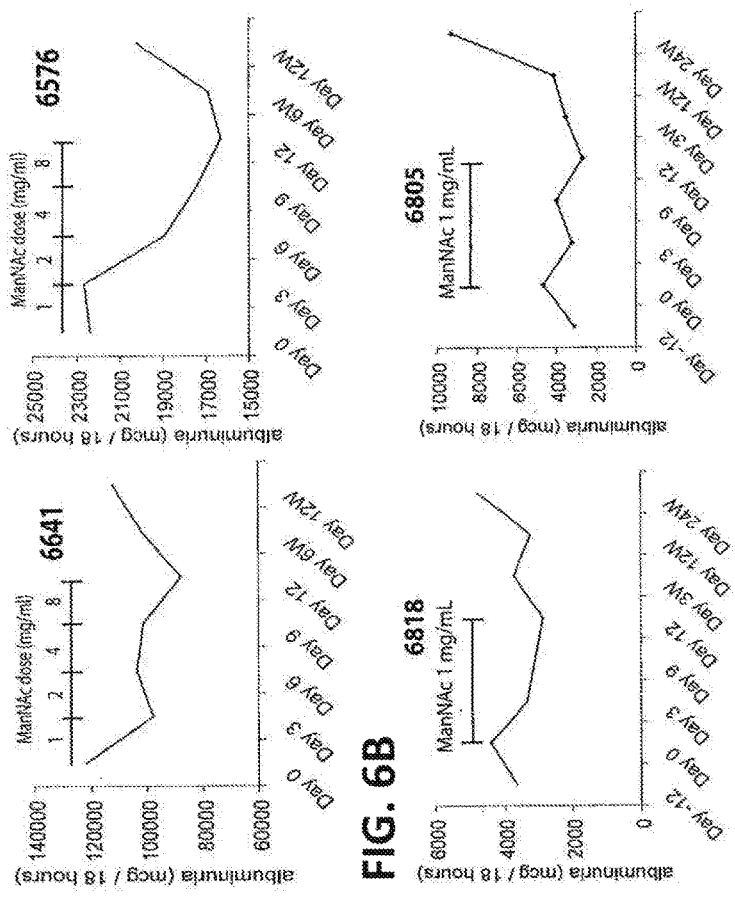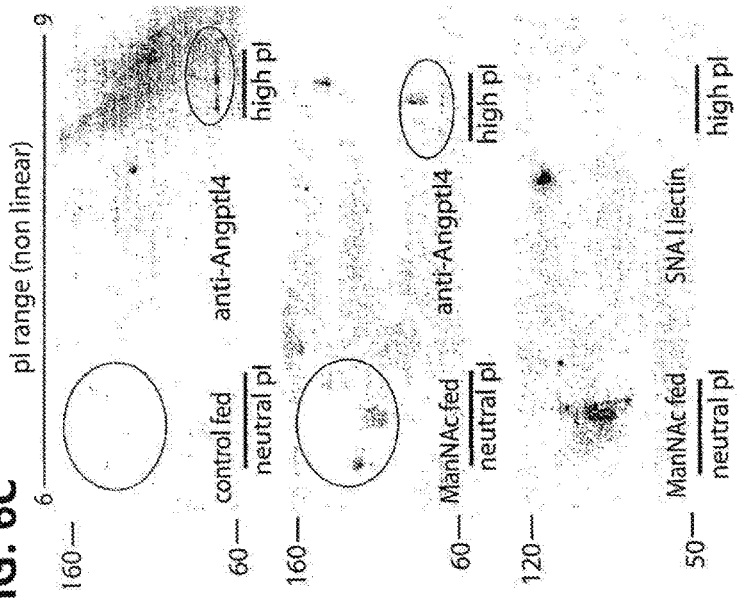
FIG. 6A
FIG. 6B
FIG. 6C
FIG. 6D

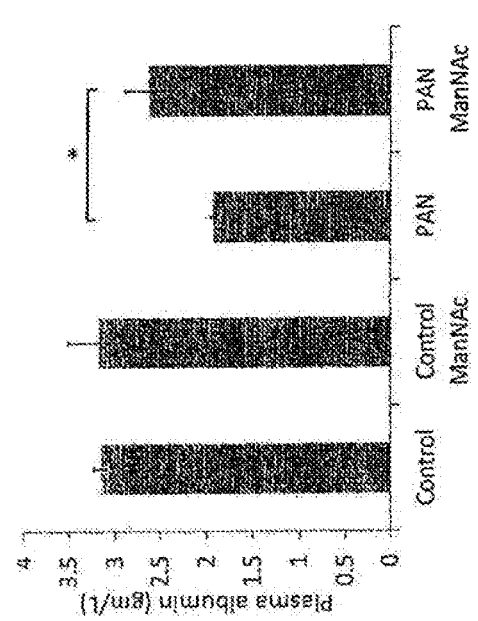
FIG. 7A
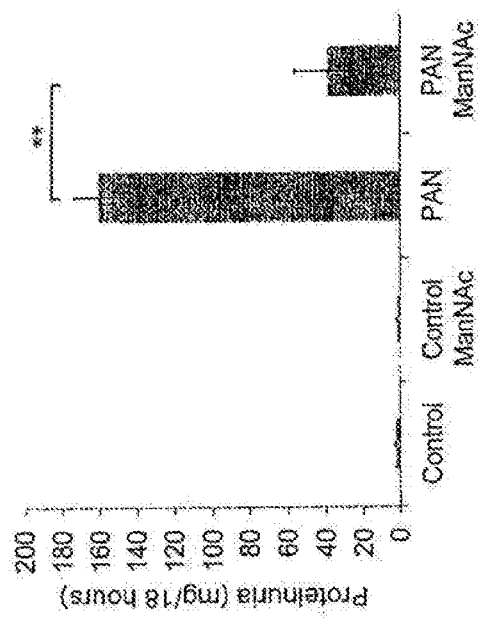
FIG. 7B
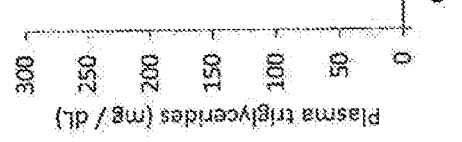
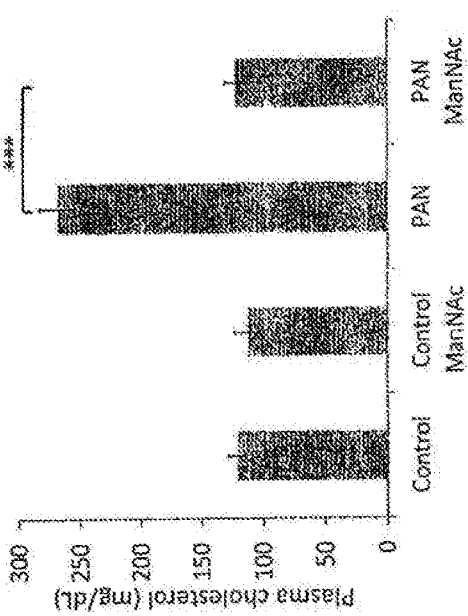
FIG. 7C
FIG. 7D

FIG. 9A

SEQ ID NO: 1

```
MSGAPTAGAA LMLCAATAVL LSAQGGPVQS KSPRFASWDE MNVLAHGLLQ LGQGLREHAE    60
RTRSQLSALE RRLSACGSAC QGTEGSTDLP LAPESRVDPE VLHSLQTQLK AQNSRIQQLF   120
HKVAQQQRHL EKQHLRIQHL QSQFGLLDHK HLDHEVAKPA RRKRLPEMAQ PVDPAHNVSR   180
LHHGGWTVIQ RRHDGSVDFN RPWEAYKAGF GDPHGEFWLG LEKVHSITGD RNSRLAVQLR   240
DWDGNAELLQ FSVHLGGEDT AYSLQLTAPV AGQLGATTVP PSGLSVPFST WDQDHDLRRD   300
KNCAKSLSGG WWFGTCSHSN LNGQYFRSIP QQRQKLKKGI FWKTWRGRYY PLQATTMLIQ   360
PMAAEAAS                                                            368
```

SEQ ID NO: 2

```
ataaaaaccg tcctcgggcg cggcggggag aagccgagct gagcggatcc tcacacgact    60
gtgatccgat tctttccagc ggcttctgca accaagcggg tcttaccccc ggtcctccgc   120
gtctccagtc ctcgcacctg gaacccaac gtcccgaga gtcccgaat cccgctcc        180
aggctaccta agaggatgag cggtgctccg acggccgggg cagccctgat gctctgcgcc   240
gccaccgccg tgctactgag cgctcagggc ggaccgtgc agtccaagtc gccgcgcttt    300
gcgtcctggg acgagatgaa tgtcctggcg cacggactcc tgcagctcgg ccaggggctg   360
cgcgaacacg cggagcgcac ccgcagtcag ctgagcgcgc tggagcggcg cctgagcgcg   420
tgcgggtccg cctgtcaggg aaccgagggg tccaccgacc tcccgttagc cctgagagc    480
cgggtggacc ctgaggtcct tcacagcctg cagacacaac tcaaggctca gaacagcagg   540
atccagcaac tcttccacaa ggtggccaac cagagcggc acctggagaa gcagcacctg   600
cgaattcagc atctgcaaag ccagtttggc ctcctggacc acaagcacct agaccatgag   660
gtggccaagc ctgccgaag aaagaggctg cccgagatgg cccagccagt gaccccggct   720
cacaatgtca gccgcctgca ccggctgccc agggattgcc aggagctgtt ccaggttggg   780
gagaggcaga gtggactatt tgaaatccag cctcaggggt ctccgccatt tttggtgaac   840
tgcaagatga cctcagatgg aggctggaca gtaattcaga ggcgcacga tggctcagtg    900
gacttcaacc ggccctggga agcctacaag gcggggtttg gggatcccca cggcgagttc   960
tggctgggtc tggagaaggt gcatagcatc acggggacc gcaacagccg cctgccgtg    1020
cagctgcggg actgggatgg caacgccgag ttgctgcagt tctccgtgca cctgggtggc  1080
gaggacacgg cctatagcct gcagctcact gcaccgtgg ccggccagct gggcgccacc   1140
accgtcccac ccagcggcct ctccgtaccc ttctccactt gggaccagga tcacgacctc   1200
cgcagggaca agaactgcgc caagagcctc tctggagct ggtggttgg cacctgcagc    1260
cattccaacc tcaacggcca gtacttccgc tccatccac agcagcggca gaagcttaag   1320
aagggaatct tctggaagac ctggcgggc cgctactacc cgctgcaggc caccaccatg   1380
ttgatccagc ccatggcagc agaggcagcc tctagcgtc ctggctgggc ctggtccag    1440
gcccacgaaa gacggtgact cttggctctg cccgaggatg tggccgttcc ctgcctgggc   1500
aggggctcca aggagggcc atctgaaaac ttgtggacag agaagaagac cacgactgga   1560
gaagccccct tctgagtgc aggggggctg catgcgttgc ctcctgagat cgaggctgca   1620
ggatatgctc agactctaga ggcgtggacc aaggggcatg gagcttcact ccttgctggc   1680
cagggagttg gggactcaga gggaccactt ggggccagcc agactggcct caatggcgga   1740
ctcagtcaca ttgactgacg gggaccaggg cttgtgtggg tcgagagcgc cctcatggtg   1800
ctggtgctgt tgtgtgtagg tccctgggg acacaagcag gcgccaatgg tatctgggcg   1860
gagctcacag agttcttgga ataaaagcaa cctcagaaca cttaaaaaaa aaaaaaaaa    1920
aaaaaaaaaa aaaaaaaaaa aaaaaaaaaa aaaaaaaaaa aaaaaaa                 1967
```

SEQ ID NO: 3

```
MSGAPTAGAA LMLCAATAVL LSAQGGPVQS KSPRFASWDE MNVLAHGLLQ LGQGLREHAE    60
RTRSQLSALE RRLSACGSAC QGTEGSTDLP LAPESRVDPE VLHSLQTQLK AQNSRIQQLF   120
HKVAQQQRHL EKQHLRIQHL QSQFGLLDHK HLDHEVAKPA RRKRLPEMAQ PVDPAHNVSR   180
LHHGGWTVIQ RRHDGSVDFN RPWEAYKAGF GDPHGEFWLG LEKVHSITGD RNSRLAVQLR   240
DWDGNAELLQ FSVHLGGEDT AYSLQLTAPV AGQLGATTVP PSGLSVPFST WDQDHDLRRD   300
KNCAKSLSGG WWFGTCSHSN LNGQYFRSIP QQRQKLKKGI FWKTWRGRYY PLQATTMLIQ   360
PMAAEAAS                                                            368
```

SEQ ID NO: 4

```
ataaaaaccg tcctcgggcg cggcggggag aagccgagct gagcggatcc tcacacgact    60
gtgatccgat tctttccagc ggcttctgca accaagcggg tcttaccccc ggtcctccgc   120
gtctccagtc ctcgcacctg gaacccaac gtcccgaga gtcccgaat cccgctcc        180
aggctaccta agaggatgag cggtgctccg acggccgggg cagccctgat gctctgcgcc   240
gccaccgccg tgctactgag cgctcagggc ggaccgtgc agtccaagtc gccgcgcttt    300
gcgtcctggg acgagatgaa tgtcctggcg cacggactcc tgcagctcgg ccaggggctg   360
cgcgaacacg cggagcgcac ccgcagtcag ctgagcgcgc tggagcggcg cctgagcgcg   420
tgcgggtccg cctgtcaggg aaccgagggg tccaccgacc tcccgttagc cctgagagc    480
```

FIG. 9B

```
cgggtggacc ctgaggtcct tcacagcctg cagacacaac tcaaggctca gaacagcagg    540
atccagcaac tcttccacaa ggtggccagc cagcagcggc acctggagaa gcagcacctg    600
cgaattcagc atctgcaaag ccagtttggc ctcctggacc acaagcacct agaccatgag    660
gtggccaagc ctgccgaag aaagaggctg cccgagatgg cccagccagt tgaccggct     720
cacaatgtca gccgcctgca ccatggaggc tggacagtaa ttcagaggcg ccacgatggc    780
tcagtggact tcaaccggcc ctgggaagcc tacaaggcgg ggtttgggga tcccacggc     840
gagttctggc tgggtctgga aaggtgcat agcatcacgg gggacgcaa cagccgcctg      900
gccgtgcagc tgcgggactg ggatggcaac gccgagttgc tgcagttctc cgtgcacctg    960
ggtggcgagg acacggccta tagcctgcag ctcactgcac ccgtggcgg ccagctgggc    1020
gccaccaccg tcccacccag cggcctctcc gtaccctcc ccacttggga ccaggatcac    1080
gacctccgca gggacaagga ctgcgccaag agcctctctg gaggctggtg gtttggcacc   1140
tgcagccatt ccaacctcaa cggccagtac ttccgctcca tccacagca gcggcagaag   1200
cttaagaagg gaatctctg gaagacctgg cggggcgct actaccgct gcaggccacc     1260
accatgttga tccagcccat ggcagcagag gcagcctcct agcgtcctgg ctgggcctgg    1320
tcccaggccc acgaaagacg gtgactcttg gctctgcccg aggatgtggc cgttcctgc    1380
ctgggcaggg gctccaagga ggggccatct ggaaacttgt ggacagagaa gaagaccacg   1440
actggagaag ccccctttct gagtgcaggg gggctgcatg cgttgcctgc tgagatcgag   1500
gctgcaggat atgctcagac tctagaggcg tggaccaagg ggcatggcg ttcactcctt    1560
gctggccagg gagttgggga ctcagaggga ccacttgggg ccagccagac tggcctcaat    1620
ggcggactca gtcacattga ctgacgggga ccagggcttg tgtgggtcga gagcgccctc   1680
atggtgctgg tgctgttgtg tgtaggtccc ctgggacac aagcaggcgc caatggtatc    1740
tgggcggagc tcacagagtt cttggaataa agcaacctc agaacactta aaaaaaaaaa    1800
aaaaaaaaaa aaaaaaaaaa aaaaaaaaaa aaaaaaaaaa aaaaaaaaaa aaa           1853
```

SEQ ID NO: 5
```
MRCAPTAGAA LVLCAATAGL LSAQGRPAQP EPPRFASWDE MNLLAHGLLQ LGHGLREHVE     60
RTRGQLGALE RRMAACGNAC QGPKGTDPKD RVPEGQAPET LQSLQTQLKA QNSKIQQLFQ    120
KVAQQQRYLS KQNLRIQNLQ SQIDLLTPTH LDNGVDKTER GKRLPKMAQL IGLTPNATRL   180
HRPPRDCQEL FQEGERHSGL FQIQPLGSPP FLVNCEMTSD GGWTVIQRRL NGSVDFNQSW    240
EAYKDGFGDP QGEFWLGLEK MHSITGDRGS QLAVQLQDWD GNAKLLQFPI HLGGEDTAYS   300
LQLTEPTANE LGATNVSPNG LSLPFSTWDQ DHDLRGDLNC AKSLSGGWWF GTCSHSNLNG   360
QYFHSIPRQR QQRKKGIFWK TWKGRYYPLQ ATTLLIQPME ATAAS                    405
```

SEQ ID NO: 6
```
atgcgctgcg ctccgaccgc aggcgctgct ctagtgctat gcgcagctac tgcggggctg     60
ctgagcgcgc aagggcgccc tgcacagccg gagccgccgc gcttcgcatc ctgggatgaa    120
atgaacttgc tggctcacgg gctgctgcag ctcggtcacg ggctgcggga cacgtggag     180
cgcaccgtg gacagctggg cgcgctggaa cgccgcatgg ctgctgcgg taacgcttgt      240
cagggggcca agggacaga cccgaaggat agagtcccg aaggccagge tcctgagact      300
ctgcagagtt tacagactca actcaaggct cagaacagca agatccagca actgttccag    360
aaggtagcc agcagcagag atacctatca aagcagaatc tgagaataca gaatcttcag    420
agccagattg acctcttgac cccacacac ctagacaatg gggtagacaa gacttcgagg    480
ggaagaggc ttcccaagat ggccagctc attggcttga ctccaacgc caccgctta      540
cacaggcctc ccgggactg ccaggaactc tttcaagaag gggagcggca cagtggactt   600
ttccagatcc agcctctggg atctccacca tttttggtca actgtgagat gacttcagat   660
ggaggctgga cggtgattca gagacgctg aacggctctg tggacttcaa tcagtcttgg   720
gaagcctaca agatggcctt cggagatccc caagtcgagt tctggctggg gctagagaag   780
atgcacagca tcacagggga ccgaggaagc cagtcgctgc tgcagctcca ggactgggat   840
ggcaatgcca aattgctcca atttcctatc catttgggg gtgaggacac agcctacagc   900
ctgcagctca ccgagccac ggccaatgag ctgggtgcca ccaatgtttc cccaatggc    960
cttttccctgc ccttctctac ctgggaccaa gaccacgacc tccgaggga ccttactgt   1020
gccagagcc tctctggtgg ctggtggttt ggcacctgca gccattccaa tctaaatgga   1080
caatacttcc actctattcc acgcaacgg cagcagcgta aaagggat cttctggaaa    1140
acatggaagg gccgctacta tccactacag gctacccacc tgttgatcca gcccatggag   1200
gctacagcag cctcttag                                                 1218
```

SEQ ID NO: 7
```
MRCAPTAGAA LVLCAATAGL LSAQGRPAQP EPPRFASWDE MNLLAHGLLQ LGHGLREHVE     60
RTRGQLGALE RRMAACGNAC QGPKGKDAPF KDSEDRVPEG QTFETLQSLQ TQLKAQNSKI   120
QQLFQKVAQQ QRYLSKQNLR IQNLQSQIDL LAPTHLDNGV DKTSRGKRLP KMTQLIGLTP   180
NATHLHRPPR DCQELFQEGE RHSGLFQIQP LGSPPFLVNC EMTSDGGWTV IQRRLNGSVD   240
FNQSWEAYKD GFGDPQGEFW LGLEKMHSIT GNRGSQLAVQ LQDWGNAKL LQFPIHLGGE    300
DTAYSLQLTE PTANELGATN VSPNGLSLPF STWDQDHDLR GDLNCAKSLS GGWWFGTCSH   360
SNLNGQYFHS IPRQRQERKK GIFWKTWKGR YYPLQATTLL IQPMEATAAS              410
```

METHODS FOR DETERMINING THE LEVEL OF HYPOSIALYLATION OF ANGPTL4

CROSS-REFERENCE TO RELATED APPLICATIONS

This application is a divisional application of U.S. application Ser. No. 14/943,167, filed Nov. 17, 2016, which is currently pending. U.S. application Ser. No. 14/943,167 is a continuation of U.S. application Ser. No. 13/152,169, filed on Jun. 2, 2011, now abandoned. U.S. application Ser. No. 13/152,169 claims the benefit of and priority to U.S. provisional application 61/351,865, filed on Jun. 5, 2010, now expired.

STATEMENT AS TO FEDERALLY SPONSORED RESEARCH

This invention was made with government support under grant numbers R01DK077073 awarded by the National Institutes of Health. The government has certain rights in the invention.

FIELD OF THE DISCLOSURE

The present disclosure is directed to methods for the treatment and prevention of nephrotic syndrome, diabetic conditions and conditions related thereto.

BACKGROUND

Nephrotic syndrome is caused by various disorders that damage the kidneys, particularly specialized cells called podocytes and the basement membrane of the glomerulus. Diabetic nephropathy and membranous glomerulonephritis (also called membranous nephropathy) are common causes in adults, whereas minimal change disease is the most common cause in children. Characteristics of nephrotic syndrome includes loss of protein in the urine (proteinuria), hyperlipidemia (hypercholesterolemia and hypertriglyceridemia), hypoalbuminemia (low blood albumin or protein levels) and edema. Proteinuria is defined as the presence of an excess of serum proteins in the urine. Albuminuria, a specific type of proteinuria, is a pathological condition wherein albumin is present in the urine.

Podocytes (or visceral epithelial cells) are cells in the glomerular capillary loop in the kidneys. The glomerulus filters blood, holding back large molecules such as proteins, and passing through small molecules such as water, salts, and sugar, as the first step in forming urine. The long processes, or "foot projections," of the podocytes wrap around the capillaries, and leave slits between them. Blood is filtered through these slits. Kidneys affected by nephrotic syndrome have small pores in the podocytes which are large enough to permit proteins to transit, causing proteinuria.

When protein is lost in the urine, its blood concentration decreases, allowing water to move into other areas of the body, which leads to swelling known as edema. Edema is commonly observed in the feet and legs, in the belly or abdomen (ascites), and around the eyes, but can occur anywhere, especially in response to gravity. Additionally, because of this extra fluid that stays in the body, people often gain weight, experience fatigue and may find that they urinate less often.

Many conditions are categorized as nephrotic syndromes, including minimal change disease (MCD), focal segmental glomerulosclerosis (FSGS), membranous nephropathy (MN) (also called membranous glomerulonephritis, MGN), and membranoproliferative glomerulonephritis (MPGN). For years pathologists found no changes in MCD tissue when viewing specimens under light microscopy, hence the name minimal change disease. With the advent of electron microscopy, the changes now known as the hallmarks for the disease include diffuse loss of podocyte foot processes, vacuolation of the podocyte foot processes, and growth of microvilli on the visceral epithelial cells. Diabetic nephropathy is the most common cause of nephrotic syndrome in developed countries.

Hypertriglyceridemia may occur due to changes in the activity of enzymes that degrade triglycerides, such as lipoprotein lipase (2-4).

The molecular basis of nephrotic syndrome is not known. Furthermore, the association of proteinuria and glucocorticoid sensitivity in nephrotic syndrome and the link between proteinuria and hypertriglyceridemia, two key components of nephrotic syndrome, have yet to be established. Therapy designed to reduce proteinuria further complicates the study of disease mechanisms. For example, glucocorticoids used to treat proteinuria in MCD independently raise plasma triglyceride levels (5), and normalization of plasma triglyceride levels lags behind the response of proteinuria to glucocorticoids in certain forms of nephrotic syndrome, such as MCD (6).

The present disclosure provides a disclosure of the biochemical basis of nephrotic syndrome (exemplified by a model of MCD) and provides an explanation for the observed proteinuria and other effects. As a result, the present disclosure provides method for treating and/or preventing nephrotic syndrome, such as but not limited to, diabetic nephropathy, MCD, FSGS, MN/MGN, and MPGN, as well as methods of alleviating symptoms associated with nephrotic syndrome, including, but not limited to, proteinuria, hypercholesterolemia, hypertriglyceridemia, hypoalbuminemia and edema. The present disclosure further provides methods for treating and preventing diabetic conditions and physiological effects thereof.

BRIEF DESCRIPTION OF THE DRAWINGS

FIGS. 1A-1I show Angptl4 mRNA and protein expression in experimental and human MCD.

FIG. 1A shows induction of nephrotoxic serum (NTS) induced heterologous phase proteinuria (n=4 rats/group); *** $P<0.001$.

FIG. 1B shows glomerular Angptl4 mRNA expression was upregulated during nephrotoxic serum (NTS) induced heterologous phase proteinuria shown in FIG. 1A (n=4 rats/group); *** $P<0.001$.

FIG. 1C shows NTS injected Angptl4 −/− mice (n=4 mice/group) develop significantly lower albuminuria, indicating a role of Angptl4 in the disease process; * $P<0.05$.

FIG. 1D shows NTS injected Angptl4 −/− mice (n=4 mice/group) developed only 30% foot process effacement compared to diffuse effacement in Angptl4 +/+ mice.

FIG. 1E shows by confocal imaging that Angptl4 in normal rat glomeruli co-localized with podocyte protein CD2AP, indicating expression in podocytes. Absorbing out reactivity from anti-Angptl4 antibody with recombinant Angptl4 abolished immunoreactivity.

FIG. 1F shows significant glomerular mRNA upregulation of Angptl4 was seen after injection of a single dose of puromycin aminonucleoside (PAN model) starting on Day 3 (peak up to 80 fold increase in different studies). Lesser upregulation developed in PHN, and no significant change was detected in anti-Thy1.1 nephritis or a rat model of non-HIV collapsing focal and segmental glomerulosclerosis (CG) using sieved glomeruli or glomeruli isolated by laser capture microdissection (LCM) [threshold for significance is 3-fold change (7)].

FIG. 1G shows glomeruli had increased Angptl4 expression (red) that overlapped partially (white arrows) with GBM heparan sulfate proteoglycans (white, intensity reduced in PAN) and podocyte nephrin (green) on day 6 after injection of a single dose of puromycin aminonucleoside (PAN model).

FIG. 1H shows Immunogold EM of PAN Model day 6 kidney demonstrating gold particles in the podocyte (yellow arrows) and GBM (black arrows); magnification: EM 40,000×.

FIG. 1I shows kidney biopsies from MCD patients (n=5 patients) revealed increased glomerular expression of Angptl4 (red) that overlaps substantially with nephrin and GBM laminin, and only marginally with endothelial PECAM1 staining; magnification: light microscopy 400×.

FIGS. 2A-F show the generation and characterization of male Angptl4 transgenic rats.

FIG. 2A show a transgenic (TG) rat model for podocyte specific over expression of Angptl4 in podocytes.

FIG. 2B shows tissue specific over expression of Angptl4 mRNA (n=3 rats/group) consistent with expression in podocytes; *** $P<0.001$.

FIG. 2C shows PAS stained sections from 3 month old heterozygous TG rats (n=3 rats/group) and revealed normal morphology (magnification 400×), with prominent podocytes in NPHS2-Angptl4 TG rats (arrows).

FIG. 2D shows confocal imaging and revealed increased glomerular expression of Angptl4 protein (magnification 400×) that overlapped with podocyte nephrin (magnification 630×) and GBM laminin (magnification 630×) in NPHS2-Angptl4 TG rats (n=3 rats/group).

FIG. 2E shows that by age 5 months, diffuse foot process effacement was noted on EM in homozygous NPHS2-Angptl4 TG rats.

FIG. 2F shows immunogold EM analysis of these rats and revealed a progression from intact foot processes (FP) containing gold particle clusters and scattered GBM particles at age 1 month, to partial effacement with GBM gold particle clusters opposite to effaced foot processes (EFP) reaching up to the endothelial (ENDO) surface, and finally diffuse effacement with dense gold particle clusters in the GBM by age 5 months. Electron microscopy magnification 15,000×-40,000×.

FIGS. 3A-H show the relationship of An tl4 overexpression with proteinuria.

FIG. 3A shows female homozygous NPHS2-Angptl4 TG rats developed significant albuminuria (n=6 rats/group); * $P<0.05$;  $P<0.01$, * $P<0.001$.

FIG. 3B shows male heterozygous NPHS2-Angptl4 TG rats developed significant albuminuria (n=6 rats/group); * $P<0.05$;  $P<0.01$, * $P<0.001$.

FIG. 3C shows male homozygous NPHS2-Angptl4 TG rats developed significant albuminuria (n=6 rats/group); ** $P<0.01$.

FIG. 3D shows GelCode blue stained SDS PAGE assessment of urinary protein (3 µg/lane, except MCD remission) followed by densitometry of the bands (n=3 readings/value) and shows a predominance of albuminuria (intact albumin band at 70 kDa, arrow) in NPHS2-Angptl4 TG rats similar to human MCD.

FIG. 3E shows immunogold EM with anti-V5 antibody to specifically detect transgenic protein in 3 month heterozygous TG male rats and showed gold particles in effaced foot processes (EFP) and GBM in NPHS2-Angptl4 TG rats; EM 40,000×.

FIG. 3F shows induction of PAN in heterozygous male NPHS2-Angptl4 (low dose) worsened, proteinuria compared to wild type littermates (n=8 rats/group); * $P<0.05$;  $P<0.01$, * $P<0.001$.

FIG. 3G shows rats treated with glucocorticoids (PAN-S) on alternate days starting 1 day after induction of PAN showed transient reduction in Day 6 proteinuria (n=4 rats/group); * $P<0.05$; ** $P<0.01$, FIG. 3H is a study of glomerular gene expression from the study in 3G, and shows that Angptl4 is a glucocorticoid sensitive gene. * $P<0.05$; ** $P<0.01$ FIG. 4A shows 2D gel electrophoresis (200 µg protein/gel) and Western blot of protein from perfused glomeruli (upper panel, control; middle panel PAN; lower panel PAN plus the addition of glucocorticoid). In the control panel, analysis revealed the presence of small amounts of fragments (red arrow; 1) and monomers (yellow arrow; 2) of Angptl4, and larger amounts of low order oligomers (pink arrows; 3) of Angptl4 migrating at neutral or high pI. On PAN Day 6 (middle panel), high and neutral pI oligomeric forms were increased (pink arrow, 3; orange arrow 4), whereas treatment with glucocorticoids (see FIG. 3G) blunts this increase (lower panel). Of the Angptl4 migrating at neutral pI, fragments were reactive with anti-phosphothreonine antibodies, whereas oligomers are reactive with sialic acid binding lectin MAA (exemplified for PAN, excerpts from independent blots).

FIG. 4B shows densitometry analysis of the Western blot from FIG. 4A;  $P<0.01$; * $P<0.001$.

FIG. 4C shows 2D gel electrophoresis (150 rig protein/gel) and Western blot of proteins from Angptl4-HEK293 stable cell line incubated with control and probed with antibodies to MAA lecithin (top panel), anti Angplt4 antibodies (upper middle panel); Angptl4-HEK293 stable cell line incubated with sialic acid precursor ManNAc (25 mM) and probed with anti-Angptl4 antibodies (lower middle panel) and Angptl4-HEK293 stable cell line incubated with sialic acid precursor ManNAc (25 mM) and probed with antibodies to MAA lecithin (lower panel). Analysis of the concentrated supernatant revealed a shift from high pI forms (green arrow and line in upper middle panel) towards neutral pI forms (blue arrow in lower middle panel and lower panel), that were MAA reactive.

FIG. 4D shows that feeding NPHS2-Angptl4 TG rats with 1 mg/ml ManNAc in tap water for 12 days (d) caused a significant reduction in 18 hour albuminuria (nadir on Day 12 was 59.4±3.3% of baseline), which returned towards baseline values after 12 days of washout, and approached untreated control NPHS2-Angptl4 TG rat values on day 24 of washout (individual tracings and pilot study data in FIG. 6). In panel d, all * differences are with baseline values. * $P<0.05$;  $P<0.01$; * $P<0.001$.

FIG. 5A shows HEK293 cells stably transfected with a pcDNA-rat Angptl4-V5-His expression construct line showed 55,000 fold upregulation of Angptl4 mRNA expression compared to a control empty vector cell line. *** $P<0.001$ FIG. 5B shows Angptl4-HEK293 cells secreted mostly intact protein into the supernatant under serum free conditions (as demonstrated by 2D gel electrophoresis and Western blot with pre-immune serum and anti-Angptl4 antibodies).

FIG. 5C shows 2D gel electrophoresis of 200 ug human plasma (n=4 patients/group) and demonstrates that only in patients with MCD relapse was elevated circulating levels of the 55-70 kDa pI 8-8.5 Angptl4 protein observed (oval in MCD relapse panel). Increased circulating levels of neutral PI monomers and oligomers were observed in MCD patients in relapse (arrow in in MCD relapse panel) and monomers only in patients with MN (arrow in MN panel).

FIGS. 6A-D show administration of ManNAc reduced albuminuria in a rat model.

FIG. 6A shows representative tracing of albuminuria from pilot studies with heavily albuminuric NPHS2-Angptl4 TG rats receiving increasing doses of ManNAc (1 to 8 mg/ml). The study revealed that ManNAc reduced albuminuria in these animals.

FIG. 6B shows individual tracings from the study group of NPHS2-Angptl4 TG rats treated with ManNAc (1 mg/ml) that completed the study. Two urine collections 12 days apart were conducted prior to the start of the study to ensure that these rats developed increasing albuminuria with time. The study revealed that ManNAc (1 mg/ml) reduced albuminuria in these animals.

FIG. 6C shows 2D electrophoresis and Western blotting (200 μg protein/gel) of glomeruli from Day 12 ManNAc or control TG rats using anti-Angptl4 antibodies or lectin SNA I (n=3 blots/condition). Reproducible neutral pI Angptl4 spots are bordered by red oval (1), and high pI by green oval (2). Neutral pI spots are also reactive with sialic acid binding lectin SNA I.

FIG. 6D shows densitometry of Angptl4 spots of FIG. 6C and indicates a significant increase in the percentage of neutral pI forms in ManNAC fed rats. *** $P<0.001$.

FIGS. 7A-D show improvement in nephrotic syndrome parameters in ManNAc treated rats with puromycin aminonucleoside nephrosis (PAN model). In FIGS. 7A-7D, rats (n=5 rats/group) received a single intravenous injection of puromycin aminonucleoside (10 mg/100 gm), and were treated with ManNAC 80 mg/Kg body weight in tap water starting on Day 4, which coincides with the onset of proteinuria.

FIG. 7A shows a significant reduction in proteinuria in ManNAc treated rats on day 6 post administration of puromycin aminonucleoside. * $P<0.05$;  $P<0.01$; * $P<0.001$.

FIG. 7B shows a significant improvement in plasma albumin levels in ManNAc treated rats on day 6 post administration of puromycin aminonucleoside. * $P<0.05$; ** $P<0.01$; * * * $P<0.001$.

FIG. 7C shows a significant reduction in hypercholesterolemia in ManNAc treated rats on day 6 post administration of puromycin aminonucleoside. * $P<0.05$;  $P<0.01$; * $P<0.001$.

FIG. 7D shows a significant reduction in hypertriglyceridemia in ManNAc treated rats on day 6 post administration of puromycin aminonucleoside. * $P<0.05$;  $P<0.01$; * $P<0.001$.

FIG. 8A shows 2D gel electrophoresis and Western blot analysis of glomeruli from diabetic db/db and control db/m mice using an anti-Angptl4 Ab. The results show increased expression of Angptl4 in diabetic mouse glomeruli as compared to control, including the high p1 forms that are involved in the pathogenesis of proteinuria.

FIG. 8B shows 2D gel electrophoresis and Western blot analysis of glomeruli from Zucker Diabetic Fatty rats and control normoglycemic rats using an anti-Angptl4 Ab. The results show increased expression of Angptl4 in rat glomeruli from Zucker Diabetic Fatty rats as compared to control, including the high pI forms that are involved in the pathogenesis of proteinuria.

FIG. 8C shows ManNac treatment decreased proteinuria in Zucker Diabetic Fatty rats. 13 week old male Zucker Diabetic Fatty rats were treated with ManNAc in tap water or with plain tap water (n=4 rats/group) at 70 and 140 mg/Kg. Significant reduction in proteinuria was noted in the ManNAc treated group. * $P<0.05$; ** $P<0.01$.

FIGS. 9A-B show the amino acid and cDNA sequences of Angptl4 from various species. SEQ ID NOS. 1 and 2 show amino acid and cDNA sequence from human (Protein Variant 1 isoform a, long form; underlined amino acid sequences at a position 40 and 161-164); SEQ ID NOS. 3 and 4 show amino acid and cDNA sequence from human (Protein Variant 3 isoform b, short form; underlined amino acid sequences at a position 40 and 161-164); SEQ ID NOS. 5 and 6 show amino acid and cDNA sequence from rat; SEQ ID NOS: 7 and 8 show amino acid and cDNA from mouse.

SUMMARY OF THE DISCLOSURE

Figure 4A:
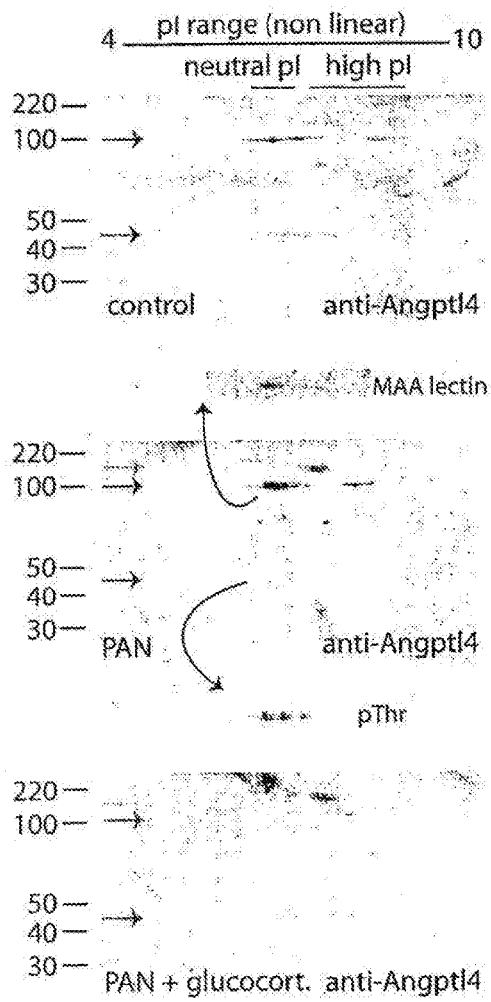
FIGS. 4A-D show the relationship of Angptl4 sialylation to proteinuria.

In a first aspect, the present disclosure provides methods of treatment and/or prevention of nephrotic syndrome in a subject. In one embodiment, the nephrotic syndrome is characterized as minimal change disease (MCD), focal segmental glomerulosclerosis (FSGS), membranous nephropathy (MN)/membranous glomerulonephritis (MGN), membranoproliferative glomerulonephritis (MPGN), and diabetic nephropathy. In another embodiment, the nephrotic syndrome is characterized as MCD. The methods comprise the step of administering to a subject sialic acid or a sialic acid precursor. The sialic acid or sialic acid precursor may be administered at a therapeutically effective dose, either alone, as a part of a pharmaceutical composition or in combination with a secondary agent. Such administration restores normal sialylation of a polypeptide, such as, but not limited to Angptl4, involved in the etiology of nephrotic syndrome, thereby treating or preventing nephrotic syndrome in the subject.

In a second aspect, the present disclosure provides methods of treatment and/or prevention of MCD in a subject. The methods comprise the step of administering to a subject a sialic acid or sialic acid precursor. The sialic acid or sialic acid precursor may be administered at a therapeutically effective dose, either alone, as a part of a pharmaceutical composition or in combination with a secondary agent. Such administration restores normal sialylation of a polypeptide, such as, but not limited to Angptl4, involved in the etiology of nephrotic syndrome, thereby treating or preventing nephrotic syndrome in the subject.

In a third aspect, the present disclosure provides methods of alleviating one or more symptoms of nephrotic syndrome, such as, but not limited to, proteinuria, hypercholesterolemia, hypertriglyceridemia and edema. In one embodiment, the nephrotic syndrome is characterized as MCD, FSGS, MN/MGN, MPGN or diabetic nephropathy. In another embodiment, the nephrotic syndrome is characterized as MCD. The methods comprise the step of administering to a subject sialic acid or a sialic acid precursor. The sialic acid or sialic acid precursor may be administered at a therapeutically effective dose, either alone, as a part of a pharmaceutical composition or in combination with a secondary agent. Such administration restores normal sialylation of a polypeptide, such as, but not limited to Angptl4, involved in the etiology of nephrotic syndrome, thereby alleviating one or more symptoms of nephrotic syndrome in the subject.

In a fourth aspect, the present disclosure provides methods for reducing proteinuria in a subject. In one embodiment, the subject is suffering from nephrotic syndrome. In one embodiment, the nephrotic syndrome is characterized as MCD, FSGS MN/MGN, MPGN or diabetic nephropathy. In another embodiment, the nephrotic syndrome is characterized as MCD. In another embodiment, the subject is suffering from a diabetic condition, such as, but not limited to, diabetic nephropathy, diabetes mellitus, lupus nephritis or primary glomular disease. In a specific embodiment, the proteinuria is caused by hyposialylation of a polypeptide, such as, but not limited to, Angptl4. The methods comprise the step of administering to a subject sialic acid or a sialic acid precursor. The sialic acid or sialic acid precursor may be administered at a therapeutically effective dose, either alone, as a part of a pharmaceutical composition or in combination with a secondary agent. Such administration restores normal sialylation of a polypeptide, such as, but not limited to Angptl4, involved in the induction of proteinuria thereby reducing proteinuria in the subject.

In a fifth aspect, the present disclosure provides methods of reducing edema in a subject. In one embodiment, the subject is suffering from nephrotic syndrome. In one embodiment, the nephrotic syndrome is characterized as MCD, FSGS, MN/MGN, MPGN or diabetic nephropathy. In another embodiment, the nephrotic syndrome is characterized as MCD. In a specific embodiment, the edema is caused by hyposialylation of a polypeptide, such as, but not limited to, Angptl4. The methods comprise the step of administering to a subject sialic acid or a sialic acid precursor. The sialic acid or sialic acid precursor may be administered at a therapeutically effective dose, either alone, as a part of a pharmaceutical composition or in combination with a secondary agent. Such administration restores normal sialylation of the polypeptide, such as, but not limited to Angptl4, involved in the induction of edema thereby reducing edema in the subject.

In a sixth aspect, the present disclosure provides methods of reducing hypercholesterolemia in a subject. In one embodiment, the subject is suffering from nephrotic syndrome. In one embodiment, the nephrotic syndrome is characterized as MCD, FSGS, MN/MGN, MPGN or diabetic nephropathy. In another embodiment, the nephrotic syndrome is characterized as MCD. In a specific embodiment, the hypercholesterolemia is caused, at least in part, by hyposialylation of a polypeptide, such as, but not limited to, Angptl4. The methods comprise the step of administering to a subject sialic acid or a sialic acid precursor. The sialic acid or sialic acid precursor may be administered at a therapeutically effective dose, either alone, as a part of a pharmaceutical composition or in combination with a secondary agent. Such administration restores normal sialylation of the polypeptide, such as, but not limited to Angptl4, involved in the induction of hypercholesterolemia thereby reducing hypercholesterolemia in the subject.

In a seventh aspect, the present disclosure provides methods of reducing hypertriglyceridemia in a subject. In one embodiment, the subject is suffering from nephrotic syndrome. In one embodiment, the nephrotic syndrome is characterized as MCD, FSGS, MN/MGN, MPGN or diabetic nephropathy. In another embodiment, the nephrotic syndrome is characterized as MCD. In a specific embodiment, the hypertriglyceridemia is caused by hyposialylation of a polypeptide, such as, but not limited to, Angptl4. The methods comprise the step of administering to a subject sialic acid or a sialic acid precursor. The sialic acid or sialic acid precursor may be administered at a therapeutically effective dose, either alone, as a part of a pharmaceutical composition or in combination with a secondary agent. Such administration restores normal sialylation of the polypeptide, such as, but not limited to Angptl4, involved in the induction of hypertriglyceridemia thereby reducing hypertriglyceridemia in the subject.

In an eight aspect, the present disclosure provides methods of treatment and/or prevention of diabetic nephropathy, diabetes mellitus, lupus nephritis or primary glomular disease. In a specific embodiment, the foregoing conditions are caused by hyposialylation of a polypeptide, such as, but not limited to, Angptl4. The methods comprise the step of administering to a subject sialic acid or a sialic acid precursor. The sialic acid or sialic acid precursor may be administered at a therapeutically effective dose, either alone, as a part of a pharmaceutical composition or in combination with a secondary agent. Such administration restores normal sialylation of the polypeptide, such as, but not limited to Angptl4, thereby treating or preventing the foregoing conditions in the subject.

In a ninth aspect, the present disclosure provides a composition for use in the methods of the first through eight aspects. The composition comprises sialic acid or one or more sialic acid precursors. In one embodiment, the sialic acid precursor is ManNAc. In an alternate embodiment, the sialic acid precursor is a derivative of ManNAc. Such composition may contain ManNAc and one or more derivatives of ManNAc as well as a secondary agent.

In a tenth aspect, the present disclosure provides for methods of determining the status of a subject with respect to nephrotic syndrome or a diabetic condition. In one embodiment, the nephrotic syndrome is characterized as MCD, FSGS, MN/MGN, MPGN or diabetic nephropathy. In another embodiment, the nephrotic syndrome is characterized as MCD. In one embodiment, the diabetic condition is diabetic nephropathy, diabetes mellitus, lupus nephritis or primary glomular disease. In a specific embodiment, the diabetic condition is diabetic nephropathy. In one embodiment, such methods determine in the subject the level of a polypeptide associated with nephrotic syndrome or a diabetic condition, such as, but not limited to, Angptl4, the level of sialylation of a polypeptide associated with nephrotic syndrome or a diabetic condition, such as, but not limited to, Angptl4, or a combination of the foregoing. The amount and/or level of sialylation of the polypeptide as determined from the subject may be compared to corresponding amounts and levels from a subject that is diagnosed as not suffering from nephrotic syndrome or a diabetic condition (control subject). Such amounts and levels may also be compared to a reference standard. A decrease in the level of sialylation as compared to the control subject or reference standard indicates the subject is suffering from or at risk for, nephrotic syndrome or a diabetic condition; the level of sialylation may be determined with respect to the high pI form of the polypeptide (which is hyposialylated).

In an eleventh aspect, the present disclosure provides for methods of determining the efficacy of a treatment for nephrotic syndrome or a diabetic condition in a subject undergoing treatment for nephrotic syndrome or a diabetic condition. In one embodiment, the nephrotic syndrome is characterized as MCD, FSGS, MN/MGN, MPGN or diabetic nephropathy. In another embodiment, the nephrotic syndrome is characterized as MCD. In one embodiment, the diabetic condition is diabetic nephropathy, diabetes mellitus, lupus nephritis or primary glomular disease. In a specific embodiment, the diabetic condition is diabetic nephropathy. The amount and/or level of sialylation of the polypeptide as determined from the subject during treatment may be compared to corresponding amounts and/or levels from the subject prior to initiating treatment. An increase in the level of sialylation in the subject undergoing treatment as compared to the level of sialylation determined prior to initiating treatment indicates the treatment is having the desired effect; the level of sialylation may be determined with respect to the high pI form of the polypeptide (which is hyposialylated). Furthermore, the amount and/or level of the polypeptide as determined from the subject during treatment may be compared to corresponding amounts and/or levels a subject that is diagnosed as not suffering from nephrotic syndrome or a diabetic condition (control subject). Such amounts and levels may also be compared to a reference standard. A level of sialylation obtained from the subject during treatment that is equal to or approaching the level of sialylation from the control subject or reference indicates the treatment is having the desired effect; the level of sialylation may be determined with respect to the high pI form of the polypeptide (which is hyposialylated).

In a twelfth aspect, the present disclosure provides for methods of identifying a compound effective for treating or preventing nephrotic syndrome, a diabetic condition or a condition associated therewith. In one embodiment, the nephrotic syndrome is characterized as MCD, FSGS, MN/MGN, MPGN or diabetic nephropathy. In another embodiment, the nephrotic syndrome is characterized as MCD. In one embodiment, the diabetic condition is diabetic nephropathy, diabetes mellitus, lupus nephritis or primary glomular disease. In a specific embodiment, the diabetic condition is diabetic nephropathy. In general, such screening methods comprises the steps of providing an assay system (as described in more detail below) that expresses a polypeptide involved in the etiology of nephrotic syndrome or a diabetic condition, such as, but not limited to, Angptl4, introducing into the assay system a test compound to be tested and determining whether the effect of the test compound on the level of sialylation of the polypeptide.

DETAILED DESCRIPTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

While investigating the pathogenesis of nephrotic syndrome and proteinuria associated therewith, γ2-nephtotoxic serum (NTS, a serum raised against whole glomeruli), was injected into rats and a panel of differentially expressed glomerular genes was identified (7). Two genes not previously known to be involved in the pathogenesis of nephrotic syndrome and proteinuria were identified. One of these genes encoded for the transcriptional factor zinc fingers and homeoboxes 3 (ZHX3) expressed in podocytes, and has now been shown to play a key role in the pathogenesis of MCD (7). The second gene, angiopoietin-like 4, ANGPTL4, was highly upregulated in the podocyte. The expression of the ANGPTL4 gene was analyzed in animal models of human glomerular disease, including puromycin nephrosis (PAN), a model of MCD, passive Heymann nephritis (PHN), a model of membranous nephropathy (MN), and anti-Thy1.1 nephritis, a model of mesangial injury.

Angiopoietin-like proteins have been implicated in the development of hypertriglyceridemia and tumor metastasis, and are functionally distinct from the angiopoietins. Angptl4 is a PPARγ (8) and PPARα (9) target gene highly expressed in the liver and adipose tissue, strongly induced by fasting in white adipose tissue and liver, and is an apoptosis survival factor for vascular endothelial cells under normoxic conditions (10). Angptl4 is a potent inhibitor of LPL (11), inducing significant hypertriglyceridemia following intravenous injection or adenovirus-mediated expression (12, 13). Other studies showed lesser expression of Angptl4 in cardiomyocytes and skeletal muscle, and low level expression in whole kidney on Northern blot analysis (8). Recent population based studies of the ANGPTL4 gene reveals variants that affect triglyceride levels in humans (14, 15).

A role of Angptl4 in proteinuria has not been previously reported. The present disclosure shows a conclusive role of podocyte secreted Angptl4 in the etiology of in nephrotic syndrome and diabetic conditions. The present disclosure demonstrates for the first time that a large part of podocyte secreted Angptl4 in experimental one form of nephrotic syndrome is hyposialylated and that improving sialylation dramatically reduces proteinuria, edema, hypercholesterolemia and hypertriglyceridemia and normalizes electrophoretic migration of Angptl4. Angptl4 is the first glucocorticoid sensitive gene to be directly implicated in the pathogenesis of nephrotic syndrome and also the first direct link between proteinuria and hypertriglyceridemia in nephrotic syndrome. Angptl4 amino acid and cDNA sequences from human (Protein Variant 1 isoform a, long form and Protein Variant 3 isoform b, short form), rat and mouse are shown in FIG. 8.

Definitions

The terms "prevention", "prevent", "preventing", "suppression", "suppress" and "suppressing" as used herein refer to a course of action (such as administering a compound or pharmaceutical composition) initiated prior to the onset of a symptom, aspect, or characteristics of a disease or condition so as to prevent or reduce such symptom, aspect, or characteristics. Such preventing and suppressing need not be absolute to be useful.

The terms "treatment", "treat" and "treating" as used herein refers a course of action (such as administering a compound or pharmaceutical composition) initiated after the onset of a symptom, aspect, or characteristics of a disease or condition so as to eliminate or reduce such symptom, aspect, or characteristics. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a disease or condition that is preventable by a method or compound of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "therapeutically effective amount" as used herein refers to an amount of a compound, either alone or as a part of a pharmaceutical composition, that is capable of having any detectable, positive effect on any symptom, aspect, or characteristics of a disease or condition. Such effect need not be absolute to be beneficial. When referring to sialic acid or a sialic acid precursor, the term "therapeutically effective amount" refers to an amount of sialic acid or the sialic acid precursor sufficient to restore normal sialylation patterns to a polypeptide, such as, but not limited to, Angltl4 or an amount of sialic acid or the sialic acid precursor sufficient to reduce proteinuria or another symptom of nephrotic syndrome in a subject.

The term "pharmaceutically acceptable derivative" means any pharmaceutically acceptable salt, ester, salt of an ester, solvate or other derivative of sialic acid or a sialic acid precursor of the present disclosure that, upon administration to a subject, is capable of providing (directly or indirectly) sialic acid or a sialic acid precursor of the disclosure or a metabolite or residue thereof. Particularly favored derivatives are those that increase the bioavailability of sialic acid or the sialic acid precursor of the disclosure when such are administered to a subject (e.g., by allowing an orally administered compound to be more readily absorbed into the blood), enhance delivery of the sialic acid precursor to a given biological compartment, increase solubility to allow administration by injection, alter metabolism or alter rate of excretion. In one embodiment, the derivative is a prodrug.

The term "pharmaceutically acceptable salt(s)", unless otherwise indicated, includes salts of acidic or basic groups that may be present in sialic acid or the sialic acid precursor of the present disclosure.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a give value. Numerical quantities given herein are approximate unless stated otherwise, meaning that the term "about" or "approximately" can be inferred when not expressly stated.

Methods of Treatment and Prevention

The present disclosure provides methods of treatment and/or prevention of nephrotic syndrome. The present disclosure further provides methods of treatment and/or prevention of MCD. The present disclosure additionally provides methods of alleviating one or more symptoms of nephritic syndrome, such as, but not limited to, proteinuria, hypercholesterolemia, hypertriglyceridemia and edema. Still further, the present disclosure provides methods for reducing proteinuria. Further still, the present disclosure provides methods for reducing edema. The present disclosure also provides methods for reducing hypercholesterolemia and hypertriglyceridemia The present disclosure also provides methods for the treatment and/or prevention of a diabetic condition or a physiological condition associated therewith. The present disclosure additionally provides for pharmaceutical compositions comprising sialic acid or one or more sialic acid precursors or combinations of the foregoing.

In one embodiment, the teachings of the present disclosure provide for the treatment and/or prevention of nephrotic syndrome in a subject in need of such treatment or prevention. In one embodiment, the nephrotic syndrome is characterized as MCD, FSGS, MN/MGN, MPGN or diabetic nephropathy. In another embodiment, the nephrotic syndrome is characterized as MCD. Such method comprises the step of administering sialic acid or a sialic acid precursor to the subject. Such administration restores normal sialylation of a polypeptide, such as, but not limited to Angptl4, involved in the etiology of nephrotic syndrome. Such administration thereby treats and/or prevents nephrotic syndrome in the subject. The sialic acid or sialic acid precursor may be administered at a therapeutically effective amount. Furthermore, sialic acid or the sialic acid precursor may be administered alone, as a part of a pharmaceutical composition or in combination with a secondary agent. Such method may further comprise identifying a subject in need of such treatment and/or prevention.

In an alternate embodiment, the teachings of the present disclosure provide for the treatment and/or prevention of MCD in a subject in need of such treatment or prevention. Such method comprises the step of administering sialic acid or a sialic acid precursor to the subject. Such administration restores normal sialylation of a polypeptide, such as, but not limited to Angptl4, involved in the etiology of MCD. Such administration thereby treats and/or prevents MCD in the subject. The sialic acid or sialic acid precursor may be administered at a therapeutically effective amount. Furthermore, sialic acid or the sialic acid precursor may be administered alone, as a part of a pharmaceutical composition or in combination with a secondary agent. Such method may further comprise identifying a subject in need of such treatment and/or prevention.

In further embodiment, the teachings of the present disclosure provide for methods of alleviating one or more symptoms of nephrotic syndrome, such as, but not limited to, proteinuria, hypercholesterolemia, hypertriglyceridemia and edema. In one embodiment, the nephrotic syndrome is characterized as MCD, FSGS, MN/MGN, MPGN or diabetic nephroapthy. In another embodiment, the nephrotic syndrome is characterized as MCD. Such method comprises the step of administering sialic acid or a sialic acid precursor to the subject. Such administration restores normal sialylation of a polypeptide, such as, but not limited to Angptl4, involved in the etiology of nephrotic syndrome. Such administration thereby alleviates one or more symptoms of nephrotic syndrome, such as, but not limited to, proteinuria and edema, nephrotic syndrome in the subject. The sialic acid or sialic acid precursor may be administered at a therapeutically effective amount. Furthermore, sialic acid or the sialic acid precursor may be administered alone, as a part of a pharmaceutical composition or in combination with a secondary agent. Such method may further comprise identifying a subject in need of such treatment and/or prevention.

In still a further embodiment, the teachings of the present disclosure provide methods for reducing proteinuria in a subject. In one embodiment, the subject is suffering from nephrotic syndrome. In one embodiment, the nephrotic syndrome is characterized as MCD, FSGS, MN/MGN, MPGN or diabetic nephroapthy. In another embodiment, the nephrotic syndrome is characterized as MCD. In another embodiment, the subject is suffering from a disorder characterized by proteinuria, such as, but not limited to, diabetic nephropathy, diabetes mellitus, lupus nephritis or primary glomular disease. In a specific embodiment, the proteinuria is caused, at least in part, by hyposialylation of a polypeptide, such as, but not limited to, Angptl4. Such method comprises the step of administering sialic acid or a sialic acid precursor to the subject. Such administration restores normal sialylation of a polypeptide, such as, but not limited to Angptl4, involved in the etiology of proteinuria. Such administration thereby reduces proteinuria in the subject. The sialic acid or sialic acid precursor may be administered at a therapeutically effective amount. Furthermore, sialic acid or the sialic acid precursor may be administered alone, as a part of a pharmaceutical composition or in combination with a secondary agent. Such method may further comprise identifying a subject in need of such reduction.

In yet a further embodiment, the teachings of the present disclosure provide methods for reducing edema in a subject. In one embodiment, the subject is suffering from nephrotic syndrome. In one embodiment, the nephrotic syndrome is characterized as MCD, FSGS, MN/MGN, MPGN or diabetic nephropathy. In another embodiment, the nephrotic syndrome is characterized as MCD. In a specific embodiment, the edema is caused, at least in part, by hyposialylation of a polypeptide, such as, but not limited to, Angptl4. Such method comprises the step of administering sialic acid or a sialic acid precursor or a combination of the foregoing to the subject. Such administration restores normal sialylation of a polypeptide, such as, but not limited to Angptl4, involved in the etiology of proteinuria. Such administration thereby reduces proteinuria in the subject. The sialic acid or sialic acid precursor may be administered at a therapeutically effective amount. Furthermore, sialic acid or the sialic acid precursor may be administered alone, as a part of a pharmaceutical composition or in combination with a secondary agent. Such method may further comprise identifying a subject in need of such reduction.

In yet a further embodiment, the teachings of the present disclosure provide methods for reducing hypercholesterolemia in a subject. In one embodiment, the subject is suffering from nephrotic syndrome. In one embodiment, the nephrotic syndrome is characterized as MCD, FSGS, MN/MGN, MPGN or diabetic nephropathy. In another embodiment, the nephrotic syndrome is characterized as MCD. In a specific embodiment, the hypercholesterolemia is caused, at least in part, by hyposialylation of a polypeptide, such as, but not limited to, Angptl4. Such method comprises the step of administering sialic acid or a sialic acid precursor to the subject. Such administration restores normal sialylation of a polypeptide, such as, but not limited to Angptl4, involved in the etiology of hypercholesterolemia. Such administration thereby reduces hypercholesterolemia in the subject. The sialic acid or sialic acid precursor may be administered at a therapeutically effective amount. Furthermore, sialic acid or the sialic acid precursor may be administered alone, as a part of a pharmaceutical composition or in combination with a secondary agent. Such method may further comprise identifying a subject in need of such reduction.

In yet a further embodiment, the teachings of the present disclosure provide methods for reducing hypertriglyceridemia in a subject. In one embodiment, the subject is suffering from nephrotic syndrome. In one embodiment, the nephrotic syndrome is characterized as MCD, FSGS, MN/MGN, MPGN or diabetic nephropathy. In another embodiment, the nephrotic syndrome is characterized as MCD. In a specific embodiment, the hypertriglyceridemia is caused, at least in part, by hyposialylation of a polypeptide, such as, but not limited to, Angptl4. Such method comprises the step of administering sialic acid or a sialic acid precursor to the subject. Such administration restores normal sialylation of a polypeptide, such as, but not limited, to Angptl4, involved in the etiology of hypertriglyceridemia. Such administration thereby reduces hypertriglyceridemia in the subject. The sialic acid or sialic acid precursor may be administered at a therapeutically effective amount. Furthermore, sialic acid or the sialic acid precursor may be administered alone, as a part of a pharmaceutical composition or in combination with a secondary agent. Such method may further comprise identifying a subject in need of such reduction.

In yet a further embodiment, the teachings of the present disclosure provide methods for treatment and/or prevention of a diabetic condition in a subject or a physiological condition associated therewith. In one embodiment, the diabetic condition is diabetic nephropathy, diabetes mellitus, lupus nephritis or primary glomular disease. In a specific embodiment, the diabetic condition is diabetic nephropathy. In one embodiment, the physiological condition associated with the diabetic condition is proteinuria. In a specific embodiment, the diabetic condition is caused, at least in part, by hyposialylation of a polypeptide, such as, but not limited to, Angptl4. Such method comprises the step of administering sialic acid or a sialic acid precursor to the subject. Such administration restores normal sialylation of a polypeptide, such as, but not limited to Angptl4, involved in the etiology of the diabetic condition. Such administration thereby treats and/or prevents the diabetic condition in the subject. The sialic acid or sialic acid precursor may be administered at a therapeutically effective amount. Furthermore, sialic acid or the sialic acid precursor may be administered alone, as a part of a pharmaceutical composition or in combination with a secondary agent. Such method may further comprise identifying a subject in need of such treatment and/or prevention.

Methods of Diagnosis

The present disclosure also provides methods for determining the status of a subject with respect to nephrotic syndrome or a diabetic condition. In one embodiment, the nephrotic syndrome is characterized as MCD, FSGS, MN/MGN, MPGN or diabetic nephropathy. In another embodiment, the nephrotic syndrome is characterized as MCD. In one embodiment, the diabetic condition is diabetic nephropathy, diabetes mellitus, lupus nephritis or primary glomular disease. In a specific embodiment, the diabetic condition is diabetic nephropathy.

In one embodiment, such methods determine in the subject the level of a polypeptide associated with nephrotic syndrome or a diabetic condition, such as, but not limited to, Angptl4, the level of sialylation of a polypeptide associated with nephrotic syndrome or a diabetic condition, such as, but not limited to, Angptl4, or a combination of the foregoing. In a particular embodiment, the level of the high pI form of the polypeptide is determined. This form has been shown to be hyposialylated and indicative of nephrotic syndrome or a diabetic condition. The amount and/or level of sialylation of the polypeptide as determined from the subject may be compared to corresponding amounts and levels from a subject that is diagnosed as not suffering from nephrotic syndrome or a diabetic condition (control subject). Such amounts and levels may also be compared to a reference standard. A decrease in the level of sialylation as compared to the control subject or reference standard indicates the subject is suffering from or at risk for, nephrotic syndrome or a diabetic condition; as discussed above, the level of sialylation may be determined with respect to the high pI form of the polypeptide (which is hyposialylated).

The present disclosure further provides methods for determining the efficacy of a treatment for nephrotic syndrome or a diabetic condition in a subject undergoing treatment for nephrotic syndrome or a diabetic condition. In one embodiment, the nephrotic syndrome is characterized as MCD, FSGS, MN/MGN, MPGN or diabetic nephropathy. In another embodiment, the nephrotic syndrome is characterized as MCD. In one embodiment, the diabetic condition is diabetic nephropathy, diabetes mellitus, lupus nephritis or primary glomular disease. In a specific embodiment, the diabetic condition is diabetic nephropathy.

In one embodiment, such methods determine in the subject the level of a polypeptide associated with nephrotic syndrome or a diabetic condition, such as, but not limited to, Angptl4, the level of sialylation of a polypeptide associated with nephrotic syndrome or a diabetic condition, such as, but not limited to, Angptl4, or a combination of the foregoing. In a particular embodiment, the level of the high pI form of the polypeptide is determined. This form has been shown to be hyposialylated and indicative of nephrotic syndrome or a diabetic condition. The amount and/or level of sialylation of the polypeptide as determined from the subject during treatment may be compared to corresponding amounts and/or levels from the subject prior to initiating treatment. An increase in the level of sialylation in the subject undergoing treatment as compared to the level of sialylation determined prior to initiating treatment indicates the treatment is having the desired effect; as discussed above, the level of sialylation may be determined with respect to the high pI form of the polypeptide (which is hyposialylated). Furthermore, the amount and/or level of the polypeptide as determined from the subject during treatment may be compared to corresponding amounts and/or levels a subject that is diagnosed as not suffering from nephrotic syndrome or a diabetic condition (control subject). Such amounts and levels may also be compared to a reference standard. A level of sialylation obtained from the subject during treatment that is equal to or approaching the level of sialylation from the control subject or reference indicates the treatment is having the desired effect; as discussed above, the level of sialylation may be determined with respect to the high pI form of the polypeptide (which is hyposialylated).

Any method known in the art for determining protein levels and levels of sialylation may be used in such methods, including, but not limited to, any methods described herein.

Figure 5C:
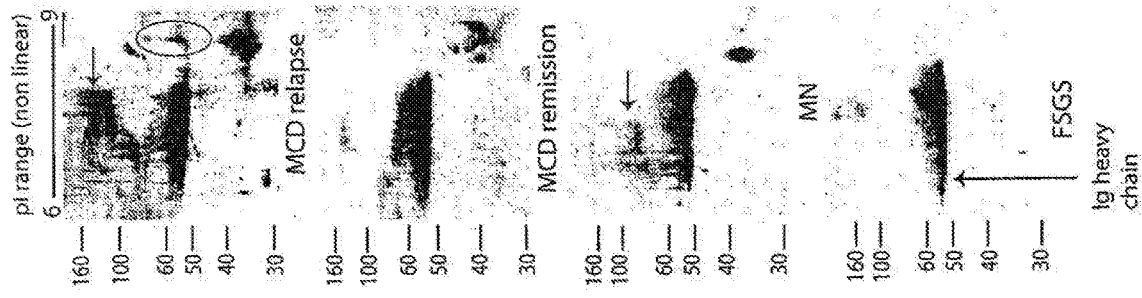
FIGS. 5A-C show characterization of recombinant Angptl4 produced by a HEK293 stable cell line.

FIG. 5C shows the utility of this approach. 200 µg human plasma from patients (n=4 patients/group) with various conditions were analyzed by 2D gel electrophoresis and Western blots were prepared using anti-Angptl4 antibodies. This figure demonstrates that only patients with MCD relapse had circulating hyposialylated form of Angptl4 polypeptide (this 55-70 kDa pI 8-8.5 form of the Angptl4 polypeptide is indicated by the oval); this polypeptide was absent in patients with MCD remission. Increased circulating neutral pI monomers and oligomers were noted in MCD patients in relapse (arrow), and monomers only in MN (arrow).

Any of the above methods of treatment may be used in conjunction with the methods of administering a polypeptide described in U.S. provisional Application Nos. 61/351,866 and 61/483,854, which are hereby incorporated by reference in their entirety.

Methods of Screening

The present disclosure also relates to a method for identifying a compound effective for treating or preventing nephrotic syndrome, a diabetic condition or a condition associated therewith, such as, but not limited to, proteinuria, hypercholesterolemia, hypertriglyceridemia or edema. In one embodiment, the nephrotic syndrome is characterized as MCD, FSGS, MN or MGN. In another embodiment, the nephrotic syndrome is characterized as MCD. In one embodiment, the diabetic condition is diabetic nephropathy, diabetes mellitus, lupus nephritis or primary glomular disease. In a specific embodiment, the diabetic condition is diabetic nephropathy. Such compounds may be useful as active ingredients included in pharmaceutical compositions or for administration alone. In one embodiment, the methods include determining the level of sialylation of a polypeptide involved in the etiology of nephrotic syndrome, such as, but not limited to, Angptl4.

In general, such screening methods comprises the steps of providing an assay system (as described in more detail below) that expresses a polypeptide involved in the etiology of nephrotic syndrome or a diabetic condition, such as, but not limited to, Angptl4, introducing into the assay system a test compound to be tested and determining whether the effect of the test compound on the level of sialylation of the polypeptide. The methods involve the identification of candidate or test compounds or agents (polypeptides, functional nucleic acids, carbohydrates, antibodies, small molecules or other molecules) which effect the level of sialylation of the polypeptide. Such compounds may then be further tested in appropriate systems (such as, but not limited to, the animal models systems described herein) to determine the activity of the identified compounds.

Candidate compounds are identified using a variety of assays, such as, but not limited to, assays that employ cells which express a polypeptide involved in the etiology of nephrotic syndrome or a diabetic condition, such as, but not limited to, Angptl4 or in assays with isolated polypeptides. The various assays can employ a variety of variants of such polypeptides (e.g., full-length, a biologically active fragment, or a fusion protein which includes all or a portion of the desired polypeptide). Moreover, such polypeptides can be derived from any suitable mammalian species (e.g., human, rat or murine); in a specific embodiment, the polypeptide is derived from a human.

Where the assay involves the use of a whole cell, the cell may either naturally express a polypeptide involved in the etiology of nephrotic syndrome or a diabetic condition, such as, but not limited to, Angptl4, or may be modified to express the same. In the latter case, cells can be modified to express a desired polypeptide through conventional molecular biology techniques, such as by infecting the cell with a virus comprising such polypeptide. The cell can also be a prokaryotic or an eukaryotic cell that has been transfected with a nucleotide sequence encoding such polypeptide. In the foregoing, full length polypeptides, fragments or fusion proteins containing at least a part of such polypeptide may be used. Exemplary assay systems are described in the current specification.

The various screening assays may be combined with an in vivo assay entailing measuring the effect of the test compound on the symptoms the disease states and conditions discussed herein. In such an embodiment, the compounds may be evaluated to determine if they impact a parameter associated with nephrotic syndrome or a diabetic condition or a condition related thereto, such as, but not limited to, proteinuria hypercholesterolemia, hypertriglyceridemia or edema. Such parameters include, but are not limited to, determining 1) the level of sialylation of a polypeptide involved in the etiology of hypercholesterolemia, reduces hypertriglyceridemia or related conditions, such as, but not limited to Angptl4 and 2) the amount of high pI forms a polypeptide involved in the etiology of hypercholesterolemia, reduces hypertriglyceridemia or related conditions, such as, but not limited to Angptl4 (these forms are hyposialylated); 3) determining the level of protein excretion, either total or with regard to specific components; and 4) determining the impact of the test compound on kidney morphology, such as, but not limited, the podocyte.

In one embodiment, such a screening assay can be performed, for example, by determining the level of sialylation of a polypeptide involved in the etiology of hypercholesterolemia, reduces hypertriglyceridemia, such as, but not limited to, Angptl4 and detecting a difference in the level of sialylation of such polypeptide in the presence of as compared to the absence of a test compound. In a particular embodiment, the high pI forms of such polypeptide are specifically examined (this form is hyposialylated). Such screening assay may be in vitro, in vivo or ex vivo and may be cell culture based (either with whole cells or lysates) or may be based on an animal model. Any assay of the present disclosure may be used in the foregoing method.

Suitable test compounds for use in the screening methods can be obtained from any suitable source, such as conventional compound libraries. The test compounds can also be obtained using any of the numerous approaches in combinatorial library methods known in the art, including: biological libraries, spatially addressable parallel solid phase or solution phase libraries, synthetic library methods requiring deconvolution, the "one-bead one-compound" library method and synthetic library methods using affinity chromatography selection. The biological library approach is limited to peptide libraries, while the other four approaches are applicable to peptide, non-peptide oligomer or small molecule libraries of compounds. Examples of methods for the synthesis of molecular libraries can be found in the art. Libraries of compounds may be presented in solution or on beads, bacteria, spores, plasmids or phage.

In the foregoing methods, the high pI forms of Angptl4 refer to a polypeptide migrating at 55-70 kDa and having a pI of 8-8.5.

The present disclosure also provides kits for carrying out any method of the present disclosure, which can contain any of the compounds and/or compositions disclosed herein or otherwise useful for practicing a method of the disclosure.

Sialic Acid Precursors

The present disclosure provides for various uses of sialic acid (N-acetylneuraminic acid) or a sialic acid precursor.

In one embodiment, the sialic acid precursor is N-acetylmannosamine (ManNAc; also referred to as 2-Acetamido-2-deoxy-D-mannose or N-acetyl-D-mannosamine). The structure of ManNAc is shown in formula I below.

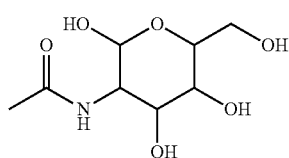

I

In an alternate embodiment, the sialic acid precursor is defined by the formula Ia below.

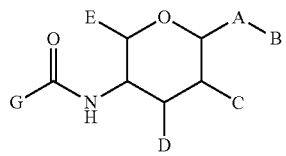

Ia

Wherein:
A is $CH_2$ or NH;
B, C, D and E are each independently selected from the group consisting of: H, OH, X, O—CO—X or O—X, wherein X is a substituted or unsubstituted alkyl or alkenyl, X (when present) being selected independently for each group B, C, D and E;
G is H, OH, Y or O—Y, wherein Y is a substituted or unsubstituted alkyl or alkenyl.

It is understood that the compounds of Formula I and Ia can also be represented in the chair configuration as well.

In one embodiment, X and/or Y are independently a C1 to C5 alkyl. In a particular embodiment, X and/or Y are propyl; in a further embodiment, X and/or Y are butyl.

In one embodiment, at least one of B, C, D, E or G is not H or OH. In a further embodiment, at least two of B, C, D, E or G is not H or OH. In still a further embodiment, at least three of B, C, D, E or G is not H or OH. In yet another embodiment, none of B, C, D, E or G is not H or OH.

In a particular embodiment, G is $CH_3$, A is $CH_2$, and at least one of B, C, D or E is not H or OH. In a further particular embodiment, G is $CH_3$, A is $CH_2$, and at least two of B, C, D or E are not H or OH. In still a further particular embodiment, G is $CH_3$, A is $CH_2$, and at least three of B, C, D or E are not H or OH. In yet a further particular embodiment, G is $CH_3$, A is $CH_2$, and all of B, C, D or E are not H or OH. In the foregoing, in one embodiment, B, C and D may each independently be CO—X.

It is noted that where G is $CH_3$, A is $CH_2$, and B, C, D and E are each OH, the compound is ManNAc (Formula I).

Representative derivatives falling under the formula I include, but are not limited to, Bu4ManNAc, 3,4,6-O-Bu3ManNAc or 1,3,4-O-Bu3ManNAc (such compounds are described in Aich, et al, Glycoconj J. DOI 10.1007/s10719-010-9292-3 accepted Apr. 14, 2010).

Additional sialic acid precursors include N-levulinoyl sialic acid (SiaLev) and N-levulinoylmannosamine (ManLev) (Charter et al. *Glycobiology*. 2000 October; 10 (10): 1049-56).

All enantiomeric fauns of the foregoing compounds are included in the above descriptions.

Compositions

Useful compositions of the present disclosure comprise one or more compounds useful in the treatment and prevention methods of the present disclosure, such as, but not limited to, sialic acid, sialic acid precursors, those compounds identified in the present disclosure or identified by a screening method of the present disclosure. In one embodiment, such compounds increase the sialylation of a polypeptide, such as, but not limited to, Angptl4. In a particular embodiment, the compounds are sialic acid precursors. Exemplary sialic acid precursors include, but are not limited to, ManNAc and ManNAc derivatives.

The compositions disclosed may comprise one or more of such compounds, in combination with a pharmaceutically acceptable carrier. Examples of such carriers and methods of formulation may be found in Remington: The Science and Practice of Pharmacy (20th Ed., Lippincott, Williams &

Wilkins, Daniel Limmer, editor). To form a pharmaceutically acceptable composition suitable for administration, such compositions will contain an therapeutically effective amount of compound.

The pharmaceutical compositions of the disclosure may be used in the treatment and prevention methods of the present disclosure. Such compositions are administered to a subject in amounts sufficient to deliver a therapeutically effective amount of the compound(s) so as to be effective in the treatment and prevention methods disclosed herein. The therapeutically effective amount may vary according to a variety of factors such as, but not limited to, the subject's condition, weight, sex and age. Other factors include the mode and site of administration. The compositions of the present disclosure may be administered only one time to the subject or more than one time to the subject. Furthermore, when the compositions are administered to the subject more than once, a variety of regimens may be used, such as, but not limited to, one per day, once per week or once per month. The compositions may also be administered to the subject more than one time per day. The therapeutically effective amount and appropriate dosing regimens may be identified by routine testing in order to obtain optimal activity, while minimizing any potential side effects. In addition, co-administration or sequential administration of other agents may be desirable.

The compositions of the present disclosure may be administered in a variety of dosage forms and regimens as discussed herein. Exemplary doses include, but are not limited to, of at least about 0.1 mg/kg to about 750 mg/kg, of at least about 1 mg/kg to about 500 mg/kg, at least about 1 mg/kg to about 200 mg/kg or at least about 1 mg/kg to about 100 mg/kg of body weight. Daily doses of a sailic acid precursor may range from about 0.1 g/day to about 75 g/day, from about 0.5 g/day to about 50 g/day, from about 1 g/day to about 10 g/day, from about 0.1 g/day to about 5 g/day, from about 0.1 g/day to about 3 g/day, and from about 0.1 g/day to about 1 g/day.

The pharmaceutical compositions may be provided to the subject in any method known in the art. Exemplary routes of administration include, but are not limited to, oral, subcutaneous, rectal, parenteral, subcutaneous, intramuscular, intraperitoneal, intravenous, topical, epicutaneous, intraosseous, intramuscular, dermal, transdermal, intrathoracic, intrapulmonary, intranasal or pulmonary routes The compositions of the present disclosure may further comprise agents which improve the solubility, half-life, absorption, etc. of the compound(s). Furthermore, the compositions of the present disclosure may further comprise agents that attenuate undesirable side effects and/or or decrease the toxicity of the compounds(s). Examples of such agents are described in a variety of texts, such a, but not limited to, Remington: The Science and Practice of Pharmacy (20$^{th}$ Ed., Lippincott, Williams & Wilkins, Daniel Limmer, editor).

The compositions of the present disclosure can be administered in a wide variety of dosage forms for administration. For example, the compositions can be administered in forms, such as, but not limited to, tablets, capsules, sachets, lozenges, troches, pills, powders, granules, elixirs, tinctures, solutions, suspensions, elixirs, syrups, ointments, creams, pastes, emulsions, or solutions for intravenous administration or injection. Other dosage forms include administration transdermally, via patch mechanism or ointment. Any of the foregoing may be modified to provide for timed release and/or sustained release formulations.

In the present disclosure, the pharmaceutical compositions may further comprise a pharmaceutically acceptable carriers include, but are not limited to, vehicles, adjuvants, surfactants, suspending agents, emulsifying agents, inert fillers, diluents, excipients, wetting agents, binders, lubricants, buffering agents, disintegrating agents and carriers, as well as accessory agents, such as, but not limited to, coloring agents and flavoring agents (collectively referred to herein as a carrier). Typically, the pharmaceutically acceptable carrier is chemically inert to the active compounds and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

For instance, for oral administration in solid form, such as but not limited to, tablets, capsules, sachets, lozenges, troches, pills, powders, or granules, the compound(s) may be combined with an oral, non-toxic pharmaceutically acceptable inert carrier, such as, but not limited to, inert fillers, suitable binders, lubricants, disintegrating agents and accessory agents. Suitable binders include, without limitation, starch, gelatin, natural sugars such as glucose or betalactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

For oral liquid forms, such as but not limited to, tinctures, solutions, suspensions, elixirs, syrups, the nucleic acid molecules of the present disclosure can be dissolved in diluents, such as water, saline, or alcohols. Furthermore, the oral liquid forms may comprise suitably flavored suspending or dispersing agents such as the synthetic and natural gums, for example, tragacanth, acacia, methylcellulose and the like. Moreover, when desired or necessary, suitable and coloring agents or other accessory agents can also be incorporated into the mixture. Other dispersing agents that may be employed include glycerin and the like.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound(s) may be administered in a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as, but not limited to, a soap, an oil or a detergent, suspending agent, such as, but not limited to, pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkylbeta-aminopropionates, and 2-alkylimidazoline quaternary ammonium salts, and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight.

Topical dosage forms, such as, but not limited to, ointments, creams, pastes, emulsions, containing the nucleic acid molecule of the present disclosure, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage or dressing for transdermal delivery or may be applied to a bandage or dressing for delivery directly to the site of a wound or cutaneous injury.

The compound(s) of the present disclosure can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Such liposomes may also contain monoclonal antibodies to direct delivery of the liposome to a particular cell type or group of cell types.

The compound(s) of the present disclosure may also be coupled with soluble polymers as targetable drug carriers. Such polymers can include, but are not limited to, polyvinylpyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Furthermore, the sialic acid or sialic acid precursors disclosed herein can be administered as a food supplement or incorporated into food or drink items.

Results

In the following results, the methods used were those methods specified in the Methods section of the present disclosure and the references cited therein.

Upregulation of Podocyte Angptl4 Expression in Experimental and Human Glomerular Disease Angptl4 mRNA expression is upregulated (70-fold) in rat glomeruli at the peak of complement- and leukocyte-independent heterologous phase proteinuria 24 hours after injection of NTS (FIG. 1A and 1B). Injection of NTS into Angptl4 −/− mice caused significant reduction in proteinuria (FIG. 1C) and foot process effacement (FIG. 1D), suggesting a key role for Angptl4 in glomerular disease. Normal rat glomeruli express Angptl4 in a capillary loop pattern that co-localized with podocyte protein CD2AP (FIG. 1E). Further studies revealed early (Day 3, before the onset of proteinuria) and progressive upregulation of Angptl4 mRNA expression in young rats following intravenous injection of a single dose of puromycin aminonucleoside (PAN model) (FIG. 1F), and in situ hybridization confirmed upregulation in a peripheral capillary loop pattern (data not shown) without concomitant change in the proximal tubular signal. In passive Heymann nephritis, a smaller increase in Angptl4 expression was noted, starting after the onset of proteinuria (FIG. 1F). By contrast, Angptl4 mRNA expression did not change in anti-Thy1.1 nephritis, or in collapsing focal and segmental glomerulosclerosis (FIG. 1F) induced in rats by injection of sera from patients with this disease (18). Angptl4 protein expression increased dramatically in podocytes (FIG. 1G) following induction of PAN, with substantial additional overlap with the glomerular basement membrane (GBM), which was confirmed by immunogold electron microscopy (EM) (FIG. 1H). Biopsies from patients with glucocorticoid sensitive MCD and age and sex-matched controls (FIG. 1I) revealed a faint podocyte pattern in control kidney biopsies, and increased expression in the podocyte with additional GBM overlap and trace spotty overlap with the endothelium at the margins.

Podocyte Specific Overexpression of Angptl4 Results in Selective Proteinuria and Podocyte Foot Process Effacement A transgenic rat models for podocyte specific Angptl4 overexpression was developed and is shown in FIG. 2A (NPHS2-Angptl4 TG). Analysis of mRNA expression in organs that normally express Angptl4 confirmed specificity of expression (FIG. 2B). Histological assessment of 3 month old heterozygous male NPHS2-Angptl4 TG rats revealed normal appearing glomeruli with prominent podocytes (FIG. 2C) on light microscopy and increased podocyte Angptl4 expression by confocal imaging (FIG. 2D). Electron microscopy of 5 month old homozygous and most heterozygous TG rats (FIG. 2E) revealed diffuse foot process effacement. Immunogold EM of homozygous TG rats revealed a correlation between accumulation of Angptl4 in the GBM and progressive development of foot process effacement between age one to five months (FIG. 2F).

Both founder lines of NPHS2-Angptl4 TG rats developed significant albuminuria. Female homozygous and male heterozygous rats developed albuminuria as early as age 1 month (FIGS. 3A-3C). Homozygous females developed up to 100-fold, heterozygous males up to 20-fold and homozygous males over 500-fold increase in albuminuria over time. Heterozygous females were not albuminuric. Over 90% of the urinary protein comprises of intact albumin (FIG. 3D), thereby making these rats the first model for selective proteinuria. Immunogold EM using anti-V5 antibody to specifically detect transgene expressed protein revealed gold particles in the podocyte and GBM in NPHS2-Angptl4 TG rats (FIG. 3E). In keeping with the pro-proteinuric effects of podocyte secreted Angptl4, NPHS2-Angptl4 TG rats develop more proteinuria (FIG. 3F) than wild type littermates after induction of PAN. Blood pressure was significantly lower in proteinuric heterozygous NPHS2-Angptl4 rats compared to wild type controls (data not shown). As also previously published (20), proteinuria in PAN is partially glucocorticoid sensitive on day 6 (FIG. 3G), and some of this glucocorticoid sensitivity is related to Angptl4 (FIG. 3H).

Characterization of Podocyte Secreted and Recombinant Angptl4

Figure 4B:
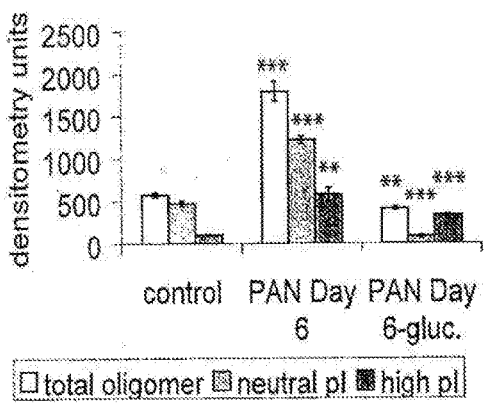

Glomerular protein Western blot typically underestimates Angptl4 production, since the protein is rapidly secreted. Angptl4 was analyzed by 2D electrophoresis and Western blotting (FIG. 4A) in glomeruli from control (upper panel), a PAN model at day 6 (middle panel) and a PAN model at day 6 with glucocorticoid coadministration (lower panel). On 2D gel electrophoresis, most Angptl4 in normal glomeruli migrates as glycosylated low order oligomers at neutral pI (pink arrow; 3), though less prominent spots for both glycosylated intact 70 KDa and cleaved (red arrow; 1) and non glycosylated 45 KDa monomeric forms (yellow arrow; 2) were also noted (FIGS. 4A and 4B). In PAN, both neutral pI oligomers, that are reactive with sialic acid binding lectin Maackia amurensis (MAA), and high pI oligomers, that are not MAA reactive, were increased (pink arrow, 3 and orange arrow, 4) (FIGS. 4A and 4B). This increase was blunted in PAN treated with glucocorticoids, though disproportionately higher amounts of high pI oligomers were noted. Densitometric analysis of the Western blots is shown in FIG. 4B.

Figure 5A:
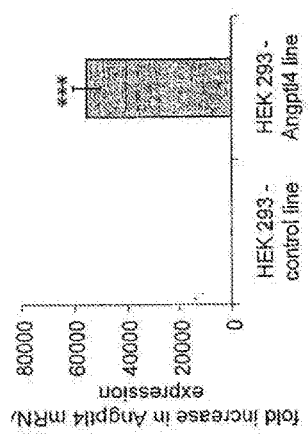

FIG. 5A shows HEK293 cells stably transfected with a pcDNA-rat Angptl4-V5-His expression construct line showed 55,000 fold upregulation of Angptl4 mRNA expression compared to a control empty vector cell line. *** P<0.001

Figure 5B:
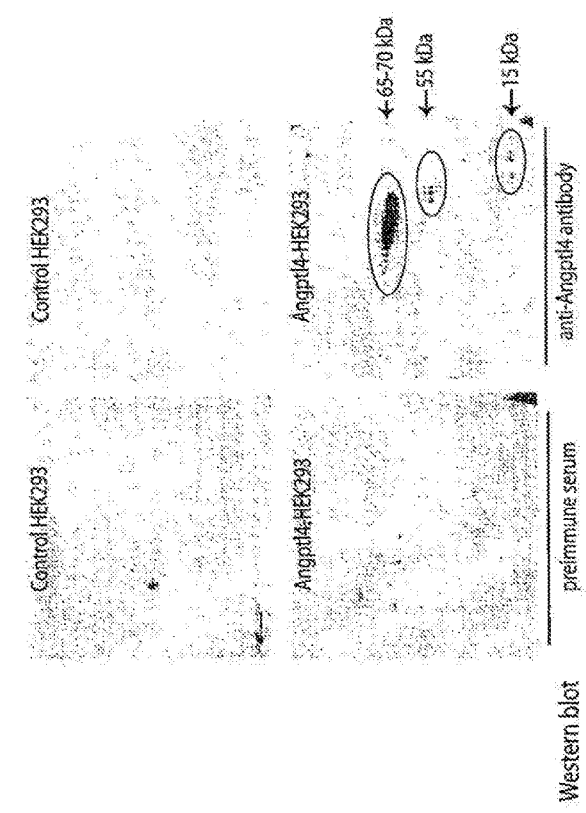

FIG. 5B shows Angptl4-HEK293 cells secreted mostly intact protein into the supernatant under serum free conditions (as demonstrated by 2D gel electrophoresis and Western blot with pre-immune serum and anti-Angptl4 antibodies).

Figure 4C:
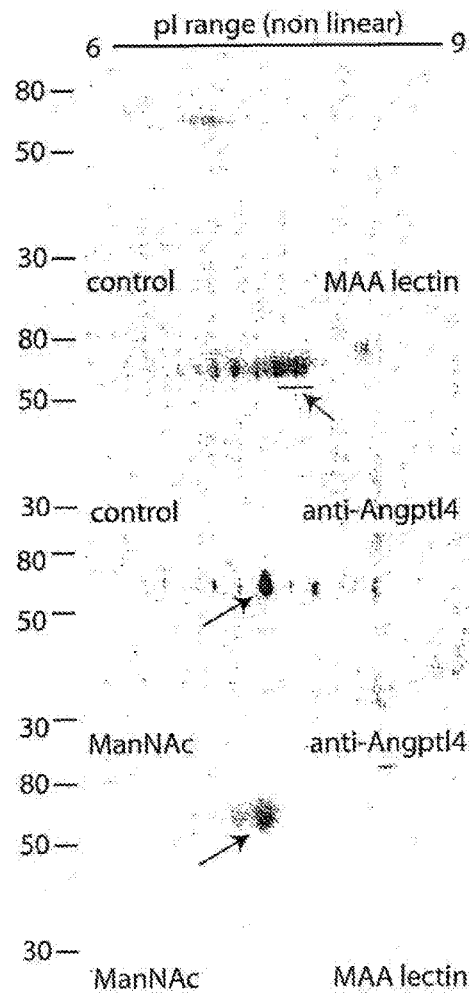

Sialylation of Angptl4 was studied in vitro (FIG. 4C) using the Angptl4-HEK293 stable cell line. HEK293 cells normally express no or little Angptl4 polypeptide; after transfection with the pcDNA-rat Angptl4-V5-His expression construct, this cell line showed a 55,000 fold upregulation of Angptl4 mRNA expression compared to a control empty vector cell line (FIG. 5A). Furthermore, the Angptl4 polypeptide expressed by the HEK293-Angptl4 cell line is normally secreted by this cell line is only trace MAA reactive at the low pI end (FIG. 4C upper panel and upper middle panel, green arrow 1 and FIG. 5B), and is therefore mostly hyposialylated. Incubation of the cell line with sialic acid precursor N-Acetyl-D-mannosamine (ManNAc; FIG. 4C, lower middle panel and lower panel) resulted in a shift of the protein towards neutral pI, increased reactivity to MAA (blue arrow, 2), and therefore, increased sialylation, showing that sialylation plays a key role in the differential electrophoretic migration of Angptl4.

Since an increase in hyposialylated Angptl4 was noted in PAN, the role of this lack of sialylation in the pathogenesis of proteinuria was studied. FIG. 6A shows representative tracing of albuminuria from pilot studies with heavily albuminuric rats receiving increasing doses of ManNAc. The study revealed that ManNAc reduced albuminuria in these animals. However, a large dose requirement to reduce albuminuria in these rats was required. In order to conduct a more efficient and indicative study, rats with 15-25 fold higher albuminuria than wild type rats were used for further analysis.

Figure 4D:
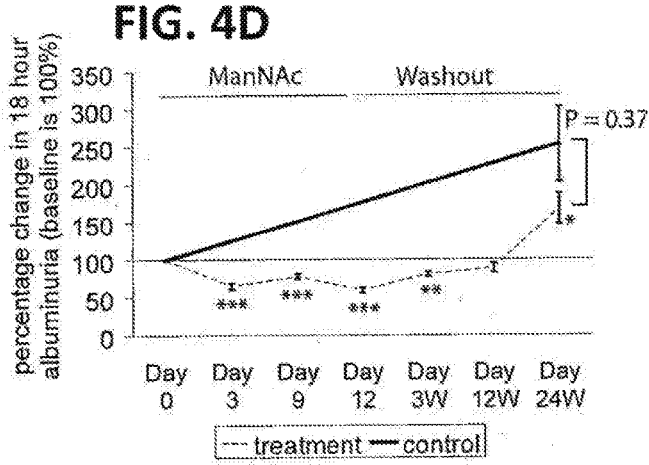

NPHS2-Angptl4 TG rats that received ManNAc (1 mg/ml) in tap water (FIG. 4D) had over 40% reduction in albuminuria over a 12 day period compared to baseline, whereas albuminuria in control NPHS2-Angptl4 TG rats receiving tap water increased 2.5 fold over the duration of the study. FIG. 6B shows individual tracings from the study group of NPHS2-Angptl4 TG rats treated with ManNAc (1 mg/ml and which went through the complete study. Two urine collections 12 days apart were conducted prior to the start of the study to ensure that these rats developed increasing albuminuria with time. The study revealed that ManNAc (1 mg/ml) reduced albuminuria in these animals.

Densitometry analysis of Western blots for glomerular Angptl4 from rats euthanized on Day 12 (FIGS. 6C and 6D) showed an increase in the neutral p1 Angptl4 fraction from 48.3+5% in control rats to 72.9+1.4% in ManNAc treated rats (FIG. 6D). The neutral pI fraction was also reactive with sialic acid binding lectin Sambucus nigra (SNA I), conforming increased sialylation of Angptl4 in ManNAc treated rats (FIG. 6C).

FIG. 7 shows improvements in nephrotic syndrome parameters in ManNAc treated rats with PAN, a model of MCD. Rats (n=5 rats/group) received a single intravenous injection of puromycin aminonucleoside (10 mg/100 gm), and were treated with ManNAC 80 mg/Kg body weight in tap water starting on Day 4, which coincides with the onset of proteinuria. Data from Day 6 is shown. Significant reduction in proteinuria (FIG. 7A), improvement in plasma albumin levels (FIG. 7B), reduction in cholesterol (FIG. 7C) and reduction in triglycerides (FIG. 7D) were noted in ManNAc treated rats when compared with control PAN rats. These data are consistent with the results described above.

Proteinuria, including albuminuria, has been noted in other diseases as discussed herein, including diabetes mellitus. The role of Angptl4 in diabetes mellitus was also analyzed using the db/db mouse. The db/db was identified initially in 1966 in Jackson Labs as an obese mouse that was hyperphagic soon on weaning. The diabetic gene (db) is transmitted as an autosomal recessive trait. The db gene encodes for a G-to-T point mutation of the leptin receptor, leading to abnormal splicing and defective signaling of the adipocyte-derived hormone leptin. Lack of leptin signaling in the hypothalamus will lead to persistent hyperphagia and obesity with consequently high leptin and insulin levels. Several studies established that albumin excretion rates are higher by 8- to 62-fold in db/db mice beginning at the age of 8 wk. The range of albuminuria is between 68 and 303 µg/24 h in the db/db male mouse, whereas it is between 4 and 21 µg/24 h in the age-matched heterozygous littermate.

Figure 8A:
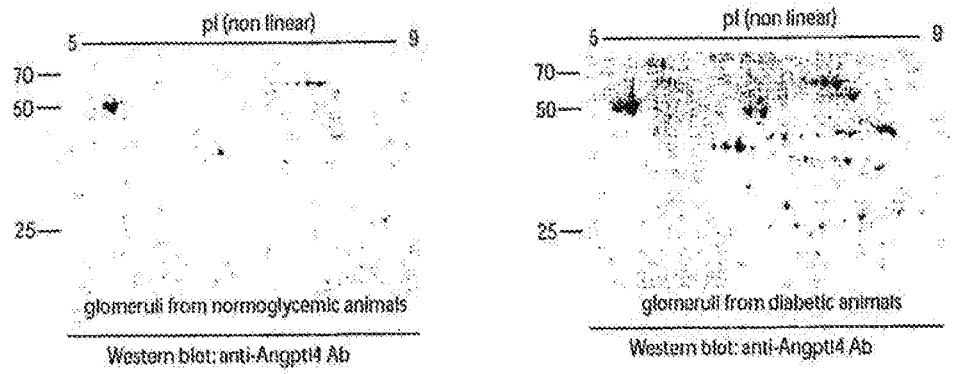
FIGS. 8A-C show the effect of ManNAc therapy on proteinuria in diabetic animals
Figure 8B:
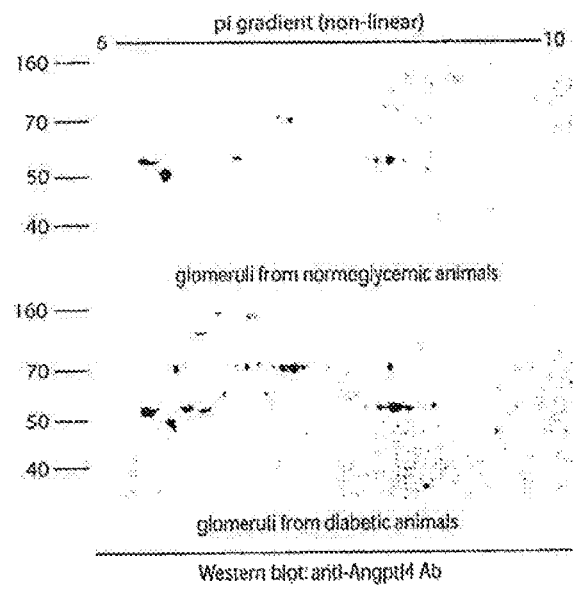
Figure 8C:
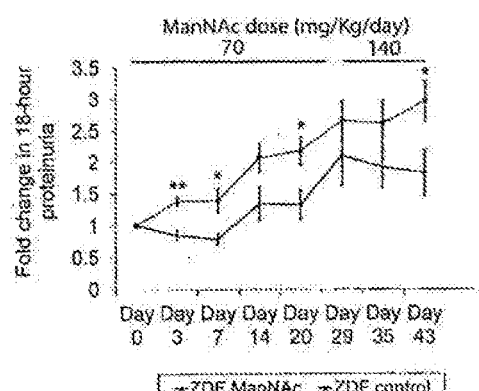

FIGS. 8A-C show the effect of ManNAc therapy on proteinuria in diabetic animals FIG. 8A shows 2D gel electrophoresis and Western blot analysis of glomeruli from diabetic db/db and control db/m mice. This analysis showed increased expression of Angptl4 in diabetic db/db mouse glomeruli, including the high pI hyposialylated forms that are involved in the pathogenesis of proteinuria. These high pI hyposialylated forms of Angptl4 are sensitive to sialic acid precursor therapy, including ManNAc and ManNAc derivatives.

FIG. 8B shows 2D gel electrophoresis and Western blot analysis of glomeruli from Zucker diabetic fatty rats. This analysis showed increased expression of Angptl4 in Zucker diabetic fatty rat glomeruli, including the high pI hyposialylated forms that are involved in the pathogenesis of proteinuria. These high pI hyposialylated forms of Angptl4 are sensitive to sialic acid precursor therapy, including ManNAc and ManNAc derivatives. FIG. 8C shows treatment with a sialic acid precursor reduced proteinuria in this model. In FIG. 8C, 13 week old male Zucker diabetic fatty rats were treated with ManNAc in tap water or with plain tap water (n=4 rats/group). Significant reduction in proteinuria was noted in the ManNAc treated group for up to 20 days at 70 mg/Kg and at an increased dose of 140 mg/Kg.

These results show that administration of sialic acid precursors treats diabetes mellitus through restoration of the normal sialyation of Angptl4. As shown in FIG. 8C, administration of sialic acid precursors reduces proteinuria observed in diabetes mellitus through restoration of normal sialylation of the Angptl4 polypeptide as described herein.

The present disclosure shows a key role of podocyte secreted Angptl4 in the pathogenesis of nephrotic syndrome, exemplified using a model of MCD and the role of Angptl4 in conditions related to nephrotic syndrome, such as, but not limited to, proteinuria. The present disclosures shows increased podocyte expression of Angptl4 in human kidney biopsies, selective proteinuria with over 500-fold increase in albuminuria in NPHS2-Angptl4 TG rats, glucocorticoid sensitivity of the Angptl4 gene, and light and electron microscopic findings consistent with human MCD. The role of Angptl4 in the development of proteinuria and foot process effacement was further confirmed by the significant reduction in proteinuria and foot process effacement in Angptl4 −/− mice injected with NTS. The absence of a reliable model of MCD in mice necessitated the use of NTS.

The secretion of high pI Angptl4 by the podocyte in MCD is likely to facilitate the tethering of Angptl4 to the GBM, and prior studies have shown the binding of Angptl4 to heparan sulfate proteoglycans (21). This correlates well with reduced GBM charge, a hallmark of MCD, in rodents with TG expression of Angptl4 from the podocyte. It is likely that charge facilitates the transit of high pI Angptl4 across the GBM against the direction of fluid flow. Changes in sialylation explain the bulk of the variations in pI and the biological role of Angptl4 in proteinuria, since the active oligomeric forms of Angptl4 secreted from podocytes were not threonine phosphorylated, and increasing the sialylation of Angptl4 reduced proteinuria. There are two predicted O- and N-glycosylation sites each in rat and human Angptl4 where sialic acid residues could be incorporated. Treatment with sialic acid precursors constitute a new potential therapeutic tool to reduce proteinuria in nephrotic syndrome, such as, but not limited to, MCD, and perhaps common multisystem disorders like diabetes mellitus, in which Angptl4 plays a role.

Additional, as yet undefined, podocyte or endothelial cell secreted factors probably work synergistically with Angptl4 in the pathogenesis of MCD. In NPHS2-Angptl4 TG rats, podocyte secreted Angptl4 remains tethered to the glomerular capillary loop or escapes into the urinary space, where it is taken up by the proximal tubule. After induction of low dose PAN in these rats, which provides these additional permeabilizing factors, podocyte secreted Angptl4 escapes into the circulation. The lack of additional permeabilizing factors in NPHS2-Angptl4 TG rats is also likely to also explain the more gradual onset of proteinuria than in PAN or patients with MCD.

The foregoing shows that administration of a sialic acid precursor restores normal sialylation of Angplt4 polypeptide and reduces physiological abnormalities associated nephrotic syndrome (including, but not limited to, MCD, FSGS, MN/MGN, MPGN or diabetic nephropathy), diabetes mellitus, lupus nephritis or primary glomular disease. As a result, the present disclosure provides a treatment for such conditions.

Methods

Cloning of Full Length Rat Angptl4, and Generation of Antibody Against Full Length Recombinant Angptl4

The full length rat Angptl4 open reading frame of 1218 bp from our previous experiments (7), excluding the stop codon, was cloned into pcDNA3.1/V5-HisB for eukaryotic expression, and into pET28a for prokaryotic expression. The E. Coli expressed purified full length protein was used to generate a polyclonal antibody in rabbits (Proteintech group, Inc. Chicago Ill. USA) that was tested by ELISA and Western blot. Antibody reactive bands were excised from GelCode blue stained gels, trypsin digested and presence of Angptl4 peptide sequences confirmed by MALDI-TOF/TOF. Part of the antiserum was affinity purified to the antigen. Unless otherwise specified, all studies described used this antibody. An additional polyclonal antibody against the N-terminal part of rat Angptl4 (amino acids 7-86 excluding signal peptide) was similarly raised in rabbits.

Induction of Proteinuria in Animal Models of Human Glomerular Disease

All animal studies were approved by the institutional IACUC. Induction of animal models of proteinuria (n=4 rats/group) in WT rats are described in previous publications in parenthesis: PAN (7), PHN (7), PAN with glucocorticoids (20), non-HIV collapsing glomerulopathy (18), nephrotoxic serum induced heterologous phase proteinuria (7); the foregoing references are hereby incorporated by reference for such teachings. Anti-Thy1.1 nephritis was induced by injection of 200 mcg of anti-Thy1.1 (Ox-7 hybridoma) or control IgG IV into different groups of male Wistar rats (100-125 gm, n=4 rats/group), and rats euthanized after 24 and 72 hours.

The following techniques are described in prior publications: Taqman real time PCR (26), confocal imaging (7), in situ hybridization (27), promoter—reporter studies (7), immunogold EM (26), glomerular extraction and processing for Western blot (26), assessment of charge by PEI method (28); the foregoing references are hereby incorproated by reference for such teachings. For alcian blue staining, the pH of the staining solution was adjusted to 2.5 using acetic acid, and 0.1% nuclear fast red solution was used as a counterstain. Densitometry of glomerular basement membrane alcian blue stain (20 glomeruli/rat, 3 rats/group) was assessed using Image-Pro software (Media Cybernetics, Inc., Bethesda Md., USA). Densitometry of 2D gel Western blots was assessed using Gel-Pro Analyzer software (Media Cybernetics, Inc.). Taqman real time PCR primers and probes are listed in Table 1. For in situ hybridization, the digoxigenin labeled probe for rat Angptl4 included bp 1 to 548 of the ORF.

To obtain samples for post heparin LPL activity, rats were injected intravenously with 10 units/100 gm weight of porcine heparin 15 minutes prior to euthanasia, and activity measured using an assay from Roar Biomedical, Inc (New York N.Y.). Serum triglycerides were measured in the fasting state.

Injection of NTS into Angptl4 −/− Mice

Angptl4 −/− mice were provided to Sander Kersten as a kind gift from Eli Lily Corporation (Indianapolis Ind. USA). The study protocol was approved by the Animal Studies Committee at Wageningen University. Eleven week old male Angptl4 −/− or +/+ mice (n=4 mice/group) were injected intravenously with 1.5 mg γ2-NTS or normal sheep serum (Sigma Aldrich St. Louis Mo. USA), spot urine samples collected, at 48 hours, mice euthanized at 72 hours, plasma collected for biochemical measurements, and kidneys preserved for histological analysis. Urine albumin was assessed by ELISA (Bethyl laboratories, Montgomery Tex. USA) and urine creatinine measured by mass spectrometry. To assess for foot process effacement, the mean width of foot processes was first measured in control treated Angptl4 +/+ mouse transmission electron micrographs (10 equally spaced readings/loop, 3 loops/glomerulus, 3 glomeruli/kidney, 3 kidneys/group). Effacement was described as an over 2.5 fold increase in mean width. Total and effaced foot processes were counted in NTS treated or control treated Angptl4 −/− mice.

Studies with Archived Human Samples

Immunostaining of archived human kidney biopsies (n=5 biopsies per condition) was conducted on samples obtained via IRB approved protocols at the Instituto Nacional de Cardiologia, Mexico City. Control kidney biopsies used for these studies were sex and age matched protocol pretransplant biopsies. Archival human sera for 2D gel electrophoresis and Western blot (n=4 samples/condition) were obtained from a previously published study (29).

Generation of Transgenic Rats:

NPHS2-Angptl4 TG rats were generated as follows: The vector pTRE-tight was digested with StuI and EcoRI to remove the minimum CMV promoter between bp 278 and 324, the 5' overhangs blunt ended with T4 DNA polymerase, and re-ligated to generate pTRE-tight MP (minus promoter). For podocyte specific expression, a rat Angptl4 cDNA construct (including the signal sequence) with a C-terminal V5 tag was placed upstream of a SV40 polyA tail. The human NPHS2 promoter was cloned upstream by PCR using a published human NPHS2 promoter construct as template (gi22652661) without DMSO to exclude a naturally occurring loop between bps 2343 and 2568 to improve expression.

Transgenic rats were generated by microinjection of the digested DNA constructs into fertilized Sprague Dawley eggs (conducted at University of Michigan), implantation into pseudopregnant host Sprague Dawley females, and the resulting offsprings were genotyped by routine PCR and TaqMan genomic DNA real time PCR strategy using construct specific and control genomic prolactin primer and probe combinations. Two founder lines for podocyte specific expression were generated. Data from NPHS2-Angptl4 TG rat line 740 (5 copies of the transgene) and were stable over 4 generations, are presented. Urinary total protein was assessed using the Bradford method (Biorad laboratories, Hercules Calif. USA), and albuminuria by ELISA (Bethyl laboratories, Montgomery Tex. USA).

Measurement of Rat Blood Pressure

Blood pressure and pulse rate were measured in six 5 month old wild type and proteinuric heterozygous NPHS2-Angptl4 TG rats by the tail cuff method using the SC-1000 apparatus from Hetteras Instruments, Inc. (Cary N.C. USA). A minimum of 80 reading were analyzed per group.

Development and Characterization of a Stable Cell Line and Recombinant Angptl4 Protein A stable cell line was developed using a rat Angptl4 pcDNA 3.1-V5/His construct, along with control empty vector stable cell lines. The Angptl4 stable cell line develops 55,253±5,155 fold rat Angptl4 mRNA upregulation (over undetectable baseline as reference value of 1) and secretes a 70 kDa protein in serum free conditions and a 55 kDa protein in the presence of serum. The full length V5-His tagged protein that was affinity purified from serum free media using a Nickel affinity column. Western blot studies performed on 2D gels revealed that most of the recombinant Angptl4 migrated as a high isoelectric point (8.3-8.5) protein, and was non-phosphorylated.

Promoter—Reporter Studies.

The mouse Angptl4 promoter previously published (31) had a transcriptional start site at −183 bp upstream of ATG in the liver. We conducted 5' RACE and primer extension analysis using mouse kidney mRNA and confirmed the same transcriptional start site in the kidney. Next, a 2 Kb fragment upstream of the transcriptional start site was clone using BAC clone RP23-27D5 as a template into pSEAP2 basic. A 2 Kb human Angptl4 promoter constructs were similarly generated using BAC clone RP11-886P16.

Incubation of HEK 293 cells and GECs transfected with Angptl4-pSEAP or empty vector promoter—reporter constructs for mouse Angptl4 with dexamethasone ($10^{-3}$ M) show a decline in SEAP activity at 48 hours. This decline in activity is mediated via the glucocorticoid receptor, since it is reversed by the receptor antagonist mifepristone ($2\times10^{-5}$ M). Glucocorticoid sensitivity of the human promoter was also assessed (dexamethasone $10^{-4}$ M). All transfection reactions were normalized using the pβgal vector (Clontech, Mountain View Calif. USA).

In vitro and in vivo Studies with ManNAc

To study the effect of manNAc on the sialylation of recombinant protein, the Angptl4-HEK293 stable or pcDNA3.1-HEK293 control stable cell lines were grown to confluence in 15 cm dishes, washed twice with warm PBS, then incubated with serum free DMEM without phenol red with or without 25 mM manNAc for 48 hours, after which the media was harvested, concentrated, protein assay conducted, and loaded on the 2D gels (200 μg/gel). Western blots of glomeruli or recombinant protein were conducted using rabbit anti-Angptl4 (full length) antibody, preimmune rabbit serum and lectins SNA I-HRP and MAA-HRP (E-Y laboratories, San Mateo Calif. USA).

Subsequent in vitro studies with neutral pI Angptl4 (ManNAc treated) or high pI Angptl4 (untreated) used either His tag purified protein or concentrated supernatant harvested from Angptl4-HEK293 stable in a same manner Control protein was concentrated from control stable cell line supernatant.

Pilot studies in heavily albuminuric NPHS2-Angptl4 rats revealed a large ManNAc dose requirement (8 mg/ml tap water) to maintain 20-30% reduction in albuminuria. To make the study affordable, 7 homozygous male NPHS2-Angptl4 rats, age 3-3.5 months, with 15-25 fold higher albuminuria than wild type rats, were given ManNAc 1 mg/ml of tap water for 12 days (ManNAc phase), after which three were euthanized and the others returned to plain tap water for another 24 days (washout phase). 18 hour urine collections were done twice (Day- 12 and Day 0) before the study to confirm rising albuminuria, and periodically during the study. Another seven male NPHS2-Angptl4 rats of similar age were assessed for baseline albuminuria levels, given normal tap water (control group), three euthanized on Day 12 and others followed up to day 36, after which albuminuria was reassessed and the animals euthanized. Daily water intake of each rat was charted. At each euthanasia time point, kidneys were removed after perfusion, glomeruli isolated and processed for 2D gel electrophoresis. Albuminuria on Day 0 for each rats was denoted as 100% and all subsequent albuminuria values were expressed relative to Day 0.

Statistical Analysis

Analysis of difference in proteinuria or gene expression involving three or more groups was conducted by ANOVA with post analysis testing using GraphPad InStat software, Version 3.05. For comparison of two groups, the unpaired Students t test in Microsoft Excel 2003 was used.

The foregoing description illustrates and describes the methods and other teachings of the present disclosure. Additionally, the disclosure shows and describes only certain embodiments of the methods and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain best modes known of practicing the methods and other teachings of the present disclosure and to enable others skilled in the art to utilize the teachings of the present disclosure in such, or other, embodiments and with the various modifications required by the particular applications or uses. Accordingly, the methods and other teachings of the present disclosure are not intended to limit the exact embodiments and examples disclosed herein. All references cited herein are incorporated by reference as if fully set forth in this disclosure.

teroid-induced alterations in hepatic production of very low density lipoprotein particles. *J. Lipid Res.* 15, 74-83 (1974).

6. Tsukamoto, Y., Kokubo, T., Horii, A., Moriya, R. & Kobayashi, Y. Lipoprotein derangement during steroid treatment in minimal-change nephrotic syndrome. *Nephron* 73, 606-612 (1996).
7. Liu, G., Clement, L., Kanwar, Y. S., Avila-Casado, C. & Chugh, S. S. ZHX proteins regulate podocyte gene expression during the development of nephrotic syndrome. *J. Biol. Chem.* 281, 39681-39692 (2006).
8. Yoon, J. C. et al. Peroxisome proliferator-activated receptor gamma target gene encoding a novel angiopoietin-related protein associated with adipose differentiation. *Mol. Cell. Biol.* 20, 5343-5349 (2000).
9. Kersten, S. et al. Characterization of the fasting-induced adipose factor FIAF, a novel peroxisome proliferator-activated receptor target gene. *J. Biol. Chem.* 275, 28488-28493 (2000).
10. Kim, I. et al. Hepatic expression, synthesis and secretion of a novel fibrinogen/angiopoietin-related protein that prevents endothelial-cell apoptosis. *Biochem. J.* 346, 603-610 (2000).
11. Yoshida, K., Shimizugawa, T., Ono, M. & Furukawa, H. Angiopoietin-like protein 4 is a potent hyperlipidemia-inducing factor in mice and inhibitor of lipoprotein lipase. *J. Lipid Res.* 43, 1770-1772 (2002).
12. Ge, H., et al. Oligomerization and regulated proteolytic processing of angiopoietin-like protein 4. *J. Biol. Chem.* 279, 2038-2045 (2004).
13. Ge, H., Yang, G., Yu, X., Pourbahrami, T. & Li, C. Oligomerization state-dependent hyperlipidemic effect of angiopoietin-like protein 4. *J. Lipid Res.* 45, 2071-2079 (2004).

TABLE 1

List of primers and probes used for Taqman real time PCR

| Gene / transgene | Forward primer | Reverse primer | Taqman probe |
| --- | --- | --- | --- |
| Angptl4 | tctgggatctccaccatttttg SEQ ID NO: 9 | tcaccgtccagcctccat SEQ ID NO: 10 | caactgtgagatgacttc SEQ ID NO: 11 |
| Angptl4 | cgccacccgcttacaca SEQ ID NO: 12 | cagaggctggatctggaaaagt SEQ ID NO: 13 | tgccaggaactctttt SEQ ID NO: 14 |
| NPHS2-Angptl4 construct | tacaggctaccaccctgttgatc SEQ ID NO: 15 | aaccgcgggccctctag SEQ ID NO: 16 | ccatggaggctacagca SEQ ID NO: 17 |
| Prolactin (genomic) | cttgaagggattgaaagataattagc SEQ ID NO: 18 | ccatgagtcagaaaagcattgaac SEQ ID NO: 19 | aggtgagcattttcctg SEQ ID NO: 20 |

REFERENCES

1. Falk R, Jennette C, Nachman P H. Primary glomerular disease. In The Kidney, Brenner B M, editor, 6th edition, 1263-1349 (2000).
2. Gutman, A. & Shafrir, E. Adipose tissue in experimental nephrotic syndrome. *Am. J. Physiol.* 205, 702-706 (1963).
3. Vaziri, N. D. Molecular mechanisms of lipid disorders in nephrotic syndrome. *Kidney Int.* 63, 1964-1976 (2003).
4. Shearer, G. C. & Kaysen G A. Endothelial bound lipoprotein lipase (LpL) depletion in hypoalbuminemia results from decreased endothelial binding, not decreased secretion. *Kidney Int.* 70, 647-653 (2006).
5. Reaven, E. P., Kolterman, O. G. & Reaven, G. M. Ultrastructural and physiological evidence for corticos- 14. Romeo, S., et al. Population-based resequencing of ANGPTL4 uncovers variations that reduce triglycerides and increase HDL. *Nat. Genet.* 39, 513-516 (2007).
15. Romeo, S. et al. Rare loss-of-function mutations in ANGPTL family members contribute to plasma triglyceride levels in humans. *J. Clin. Invest.* 119:70-79 (2009).
16. Eremina, V., et al. VEGF inhibition and renal thrombotic microangiopathy. *N. Engl. J. Med.* 358, 1129-1136 (2008).
17. Davis, B., et al. Podocyte-specific expression of angiopoietin-2 causes proteinuria and apoptosis of glomerular endothelia. *J. Am. Soc. Nephrol.* 18, 2320-2329 (2007).
18. Avila-Casado, C., et al. Proteinuria in rats induced by serum from patients with collapsing glomerulopathy. *Kidney Int.* 66, 133-143 (2004).

19. Mandard, S., et al. The fasting-induced adipose factor/angiopoietin-like protein 4 is physically associated with lipoproteins and governs plasma lipid levels and adiposity. *J. Biol. Chem.* 281:934-944 (2006).
20. Clement, L., et al. Early changes in gene expression that influence the course of primary glomerular disease. *Kidney Int.* 72, 337-347 (2007).
21. Cazes, A. et al. Extracellular matrix-bound angiopoietin-like 4 inhibits endothelial cell adhesion, migration, and sprouting and alters actin cytoskeleton. *Circ. Res.* 99, 1207-1215 (2006).
22. Malicdan, M. C., Noguchi, S., Hayashi, Y. K., Nonaka, I. & Nishino, I. Prophylactic treatment with sialic acid metabolites precludes the development of the myopathic phenotype in the DMRV-hIBM mouse model. *Nat. Med.* 15, 690-695 (2009).
23. Galeano, B. et al. Mutation in the key enzyme of sialic acid biosynthesis causes severe glomerular proteinuria and is rescued by N-acetylmannosamine. *J. Clin. Invest.* 117, 1585-1594 (2007).
24. Ruge, T. et al. Lipoprotein lipase in the kidney: activity varies widely among animal species. *Am. J. Physiol. Renal Physiol.* 287, F1131-F1139 (2004).
25. Koliwad, S. K. et al. Angiopoietin-like 4 (ANGPTL4/FIAF) is a direct glucocorticoid receptor target and participates in glucocorticoid-regulated triglyceride metabolism. *J. Biol. Chem.* 284, 25593-25601(2009).
26. Liu, G. at al. Neph1 and nephrin interaction in the slit diaphragm is an important determinant of glomerular permeability. *J. Clin. Invest.* 112, 209-221 (2003).
27. Dijkman, H. B. P. M., Mentzel, S., de Jong, A. S. & Assmann, K. J. M. RNA in situ hybridization using digoxigenin-labeled cRNA probes. *Biochemica* 2, 23-27 (1995).
28. Isogai, S., Mogami, K., Shiina, N. & Yoshino, G. Initial ultrastructural changes in pore size and anionic sites of the glomerular basement membrane in streptozotocin-induced diabetic rats and their prevention by insulin treatment. *Nephron.* 83, 53-58 (1999).
29. Bakker, W. W. et al. Altered activity of plasma hemopexin in patients with minimal change disease in relapse. *Pediatr. Nephrol.* 20, 1410-1415 (2005).
30. Graves, R. A., Tontonoz, P., Platt, K. A., Ross, S. R. & Spiegelman, B. M. Identification of a fat cell enhancer: analysis of requirements for adipose tissue-specific gene expression. *J. Cell Biochem.* 49, 219-224 (1992).
31. Yoshida, K., Ono, M., Koishi, R. & Furukawa, H. Characterization of the 5' regulatory region of the mouse angiopoietin-like protein 4. *Vet. Res. Commun.* 28, 299-305 (2004).
32. Zeng, L. et al. HMG CoA reductase inhibition modulates VEGF-induced endothelial cell hyperpermeability by preventing RhoA activation and myosin regulatory light chain phosphorylation. *FASEB J.* 19, 1845-1847 (2005).

What is claimed:

1. A method for determining the status of a subject with respect to a hyposialylated form of an angiopoietin-like 4 (Angptl4) polypeptide, said method comprising the steps of:
   a. obtaining a sample containing the Angptl4 polypeptide from the subject; and
   b. determining a level of sialylation of the Angptl4 polypeptide in the sample.

2. The method of claim 1, wherein prior to determining the level of sialylation of the Angptl4 polypeptide, the Angptl4 polypeptide in the sample is separated by isoelectric point.

3. The method of claim 2, wherein the determining step is made based on the separated Angptl4 polypeptide having an isoelectric point of 8.0 to 8.5.

4. The method of claim 1 further comprising comparing the level of sialylation of the Angptl4 polypeptide from the subject to a control value.

5. The method of claim 4, wherein the control value is a reference standard.

6. A method for determining the status of a subject with respect to a hyposialylated form of an angiopoietin-like 4 (Angptl4) polypeptide, said method comprising the steps of:
   a. obtaining a sample containing an Angptl4 polypeptide from the subject;
   b. separating the Angptl4 polypeptide in the sample by isoelectric point; and
   c. determining the level of sialylation of the Angptl4, wherein the determining step is made based on the separated Angptl4 polypeptide having an isoelectric point of 8.0 to 8.5.

7. The method of claim 6 further comprising comparing the level of sialylation of the Angptl4 polypeptide from the subject to a control value.

8. The method of claim 7, wherein the control value is a reference standard.

* * * * *

SEQUENCE LISTING

```
<160> NUMBER OF SEQ ID NOS: 20

<210> SEQ ID NO 1
<211> LENGTH: 368
<212> TYPE: PRT
<213> ORGANISM: Homo sapiens

<400> SEQUENCE: 1

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Gly Gly Trp Thr Val Ile Gln Arg Arg
```

```
                   180                 185                 190
His Asp Gly Ser Val Asp Phe Asn Arg Pro Trp Glu Ala Tyr Lys Ala
            195                 200                 205
Gly Phe Gly Asp Pro His Gly Glu Phe Trp Leu Gly Leu Glu Lys Val
        210                 215                 220
His Ser Ile Thr Gly Asp Arg Asn Ser Arg Leu Ala Val Gln Leu Arg
225                 230                 235                 240
Asp Trp Asp Gly Asn Ala Glu Leu Leu Gln Phe Ser Val His Leu Gly
                245                 250                 255
Gly Glu Asp Thr Ala Tyr Ser Leu Gln Leu Thr Ala Pro Val Ala Gly
            260                 265                 270
Gln Leu Gly Ala Thr Thr Val Pro Pro Ser Gly Leu Ser Val Pro Phe
        275                 280                 285
Ser Thr Trp Asp Gln Asp His Asp Leu Arg Arg Asp Lys Asn Cys Ala
        290                 295                 300
Lys Ser Leu Ser Gly Gly Trp Trp Phe Gly Thr Cys Ser His Ser Asn
305                 310                 315                 320
Leu Asn Gly Gln Tyr Phe Arg Ser Ile Pro Gln Gln Arg Gln Lys Leu
                325                 330                 335
Lys Lys Gly Ile Phe Trp Lys Thr Trp Arg Gly Arg Tyr Tyr Pro Leu
            340                 345                 350
Gln Ala Thr Thr Met Leu Ile Gln Pro Met Ala Ala Glu Ala Ala Ser
        355                 360                 365

<210> SEQ ID NO 2
<211> LENGTH: 1967
<212> TYPE: DNA
<213> ORGANISM: Homo sapiens

<400> SEQUENCE: 2
ataaaaaccg tcctcgggcg cggcggggag aagccgagct gagcggatcc tcacacgact      60
gtgatccgat tctttccagc ggcttctgca accaagcggg tcttaccccc ggtcctccgc     120
gtctccagtc ctcgcacctg aaccccaac gtccccgaga gtccccgaat ccccgctccc     180
aggctaccta agaggatgag cggtgctccg acggccgggg cagccctgat gctctgcgcc     240
gccaccgccg tgctactgag cgctcagggc ggacccgtgc agtccaagtc gccgcgcttt     300
gcgtcctggg acgagatgaa tgtcctggcg cacggactcc tgcagctcgg ccaggggctg     360
cgcgaacacg cggagcgcac cgcagtcag ctgagcgcgc tggagcggcg cctgagcgcg     420
tgcgggtccg cctgtcaggg aaccgagggg tccaccgacc tcccgttagc ccctgagagc     480
cgggtggacc ctgaggtcct tcacagcctg cagacacaac tcaaggctca gacagcagg     540 atccagcaac tcttccacaa ggtggcccag cagcagcggc acctggagaa gcagcacctg     600
cgaattcagc atctgcaaag ccagtttggc ctcctggacc acaagcacct agaccatgag     660
gtggccaagc tgcccgaag aaagaggctg cccgagatgg cccagccagt tgacccggct     720
cacaatgtca gccgcctgca ccggctgccc agggattgcc aggagctgtt ccaggttggg     780
gagaggcaga gtggactatt tgaaatccag cctcaggggt ctccgccatt tttggtgaac     840
tgcaagatga cctcagatgg aggctggaca gtaattcaga gcgcgcacga tggctcagtg     900
gacttcaacc ggccctggga agcctacaag gcggggtttg gggatcccca cggcgagttc     960
tggctgggtc tggagaaggt gcatagcatc acggggacc gcaacagccg cctggccgtg    1020
cagctgcggg actgggatgg caacgccgag ttgctgcagt tctccgtgca cctgggtggc    1080
```

-continued

```
gaggacacgg cctatagcct gcagctcact gcacccgtgg ccggccagct gggcgccacc    1140
accgtcccac ccagcggcct ctccgtaccc ttctccactt gggaccagga tcacgacctc    1200
cgcagggaca agaactgcgc caagagcctc tctggaggct ggtggtttgg cacctgcagc    1260
cattccaacc tcaacggcca gtacttccgc tccatcccac agcagcggca gaagcttaag    1320
aagggaatct tctggaagac ctggcggggc cgctactacc cgctgcaggc caccaccatg    1380
ttgatccagc ccatggcagc agaggcagcc tcctagcgtc ctggctgggc ctggtcccag    1440
gcccacgaaa gacggtgact cttggctctg cccgaggatg tggccgttcc ctgcctgggc    1500
aggggctcca aggaggggcc atctggaaac ttgtggacag agaagaagac cacgactgga    1560
gaagccccct ttctgagtgc agggggggctg catgcgttgc ctcctgagat cgaggctgca    1620
ggatatgctc agactctaga ggcgtggacc aagggcatg gagcttcact ccttgctggc    1680
cagggagttg gggactcaga gggaccactt ggggccagcc agactggcct caatggcgga    1740
ctcagtcaca ttgactgacg gggaccaggg cttgtgtggg tcgagagcgc cctcatggtg    1800
ctggtgctgt tgtgtgtagg tcccctgggg acacaagcag gcgccaatgg tatctgggcg    1860
gagctcacag agttcttgga ataaaagcaa cctcagaaca cttaaaaaaa aaaaaaaaa    1920 aaaaaaaaaa aaaaaaaaaa aaaaaaaaaa aaaaaaaaaa aaaaaaa    1967
```

<210> SEQ ID NO 3
<211> LENGTH: 368
<212> TYPE: PRT
<213> ORGANISM: Homo sapiens

<400> SEQUENCE: 3

```
Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Gly Gly Trp Thr Val Ile Gln Arg Arg
            180                 185                 190

His Asp Gly Ser Val Asp Phe Asn Arg Pro Trp Glu Ala Tyr Lys Ala
        195                 200                 205

Gly Phe Gly Asp Pro His Gly Glu Phe Trp Leu Gly Leu Glu Lys Val
    210                 215                 220
```

```
His Ser Ile Thr Gly Asp Arg Asn Ser Arg Leu Ala Val Gln Leu Arg
225                 230                 235                 240

Asp Trp Asp Gly Asn Ala Glu Leu Leu Gln Phe Ser Val His Leu Gly
            245                 250                 255

Gly Glu Asp Thr Ala Tyr Ser Leu Gln Leu Thr Ala Pro Val Ala Gly
        260                 265                 270

Gln Leu Gly Ala Thr Thr Val Pro Pro Ser Gly Leu Ser Val Pro Phe
    275                 280                 285

Ser Thr Trp Asp Gln Asp His Asp Leu Arg Arg Asp Lys Asn Cys Ala
290                 295                 300

Lys Ser Leu Ser Gly Gly Trp Trp Phe Gly Thr Cys Ser His Ser Asn
305                 310                 315                 320

Leu Asn Gly Gln Tyr Phe Arg Ser Ile Pro Gln Gln Arg Gln Lys Leu
                325                 330                 335

Lys Lys Gly Ile Phe Trp Lys Thr Trp Arg Gly Arg Tyr Tyr Pro Leu
            340                 345                 350

Gln Ala Thr Thr Met Leu Ile Gln Pro Met Ala Ala Glu Ala Ala Ser
        355                 360                 365
```

<210> SEQ ID NO 4
<211> LENGTH: 1853
<212> TYPE: DNA
<213> ORGANISM: Homo sapiens

<400> SEQUENCE: 4

```
ataaaaaccg tcctcgggcg cggcggggag aagccgagct gagcggatcc tcacacgact    60
gtgatccgat tctttccagc ggcttctgca accaagcggg tcttaccccc ggtcctccgc   120
gtctccagtc ctcgcacctg aaccccaac gtccccgaga gtccccgaat ccccgctccc    180
aggctaccta agaggatgag cggtgctccg acggccgggg cagccctgat gctctgcgcc   240
gccaccgccg tgctactgag cgctcagggc ggacccgtgc agtccaagtc gccgcgcttt   300
gcgtcctggg acgagatgaa tgtcctggcg cacggactcc tgcagctcgg ccaggggctg   360
cgcgaacacg cggagcgcac cgcagtcag ctgagcgcgc tggagcggcg cctgagcgcg   420
tgcgggtccg cctgtcaggg aaccgagggg tccaccgacc tcccgttagc ccctgagagc   480
cgggtggacc ctgaggtcct tcacagcctg cagacacaac tcaaggctca gaacagcagg   540
atccagcaac tcttccacaa ggtggcccag cagcagcggc acctggagaa gcagcacctg   600
cgaattcagc atctgcaaag ccagtttggc ctcctggacc acaagcacct agaccatgag   660
gtggccaagc tgcccgaag aaagaggctg cccgagatgg cccagccagt tgaccggct    720
cacaatgtca gccgcctgca ccatggaggc tggacagtaa ttcagaggcg ccacgatggc   780
tcagtggact tcaaccggcc ctgggaagcc tacaaggcgg ggtttggga tccccacggc   840
gagttctggc tgggtctga aaggtgcat agcatcacgg gggaccgcaa cagccgcctg   900
gccgtgcagc tgcgggactg ggatggcaac gccgagttgc tgcagttctc cgtgcacctg   960
ggtggcgagg acacggccta tagcctgcag ctcactgcac ccgtggccgg ccagctgggc  1020
gccaccaccg tcccacccag cggcctctcc gtacccttct ccacttggga ccaggatcac  1080
gacctccgca gggacaagaa ctgcgccaag agcctctctg gaggctggtg gtttggcacc  1140
tgcagccatt ccaacctcaa cggccagtac ttcgctcca tcccacagca gcggcagaag  1200
cttaagaagg gaatcttctg gaagacctgg cggggccgct actacccgct gcaggccacc  1260
accatgttga tccagcccat ggcagcagag gcagcctcct agcgtcctgg ctgggcctgg  1320
```

```
tcccaggccc acgaaagacg gtgactcttg gctctgcccg aggatgtggc cgttccctgc   1380
ctgggcaggg gctccaagga gggggccatct ggaaacttgt ggacagagaa aagaccacg   1440
actggagaag ccccctttct gagtgcaggg gggctgcatg cgttgcctcc tgagatcgag   1500
gctgcaggat atgctcagac tctagaggcg tggaccaagg ggcatggagc ttcactcctt   1560
gctggccagg gagttgggga ctcagaggga ccacttgggg ccagccagac tggcctcaat   1620
ggcggactca gtcacattga ctgacgggga ccagggcttg tgtgggtcga gagcgccctc   1680
atggtgctgg tgctgttgtg tgtaggtccc ctggggacac aagcaggcgc caatggtatc   1740
tgggcggagc tcacagagtt cttggaataa aagcaacctc agaacactta aaaaaaaaaa   1800
aaaaaaaaaa aaaaaaaaaa aaaaaaaaaa aaaaaaaaaa aaaaaaaaaa aaa          1853
```

<210> SEQ ID NO 5
<211> LENGTH: 405
<212> TYPE: PRT
<213> ORGANISM: Rattus norvegicus

<400> SEQUENCE: 5

```
Met Arg Cys Ala Pro Thr Ala Gly Ala Ala Leu Val Leu Cys Ala Ala
1               5                   10                  15

Thr Ala Gly Leu Leu Ser Ala Gln Gly Arg Pro Ala Gln Pro Glu Pro
            20                  25                  30

Pro Arg Phe Ala Ser Trp Asp Glu Met Asn Leu Leu Ala His Gly Leu
        35                  40                  45

Leu Gln Leu Gly His Gly Leu Arg Glu His Val Glu Arg Thr Arg Gly
    50                  55                  60

Gln Leu Gly Ala Leu Glu Arg Arg Met Ala Ala Cys Gly Asn Ala Cys
65                  70                  75                  80

Gln Gly Pro Lys Gly Thr Asp Pro Lys Asp Arg Val Pro Glu Gly Gln
                85                  90                  95

Ala Pro Glu Thr Leu Gln Ser Leu Gln Thr Gln Leu Lys Ala Gln Asn
            100                 105                 110

Ser Lys Ile Gln Gln Leu Phe Gln Lys Val Ala Gln Gln Gln Arg Tyr
        115                 120                 125

Leu Ser Lys Gln Asn Leu Arg Ile Gln Asn Leu Gln Ser Gln Ile Asp
    130                 135                 140

Leu Leu Thr Pro Thr His Leu Asp Asn Gly Val Asp Lys Thr Ser Arg
145                 150                 155                 160

Gly Lys Arg Leu Pro Lys Met Ala Gln Leu Ile Gly Leu Thr Pro Asn
                165                 170                 175

Ala Thr Arg Leu His Arg Pro Arg Asp Cys Gln Glu Leu Phe Gln
            180                 185                 190

Glu Gly Glu Arg His Ser Gly Leu Phe Gln Ile Gln Pro Leu Gly Ser
        195                 200                 205

Pro Pro Phe Leu Val Asn Cys Glu Met Thr Ser Asp Gly Gly Trp Thr
    210                 215                 220

Val Ile Gln Arg Arg Leu Asn Gly Ser Val Asp Phe Asn Gln Ser Trp
225                 230                 235                 240

Glu Ala Tyr Lys Asp Gly Phe Gly Asp Pro Gln Gly Glu Phe Trp Leu
                245                 250                 255

Gly Leu Glu Lys Met His Ser Ile Thr Gly Asp Arg Gly Ser Gln Leu
            260                 265                 270

Ala Val Gln Leu Gln Asp Trp Asp Gly Asn Ala Lys Leu Leu Gln Phe
```

```
                275                 280                 285
Pro Ile His Leu Gly Gly Glu Asp Thr Ala Tyr Ser Leu Gln Leu Thr
        290                 295                 300
Glu Pro Thr Ala Asn Glu Leu Gly Ala Thr Asn Val Ser Pro Asn Gly
305                 310                 315                 320
Leu Ser Leu Pro Phe Ser Thr Trp Asp Gln Asp His Asp Leu Arg Gly
                325                 330                 335
Asp Leu Asn Cys Ala Lys Ser Leu Ser Gly Gly Trp Trp Phe Gly Thr
            340                 345                 350
Cys Ser His Ser Asn Leu Asn Gly Gln Tyr Phe His Ser Ile Pro Arg
        355                 360                 365
Gln Arg Gln Gln Arg Lys Lys Gly Ile Phe Trp Lys Thr Trp Lys Gly
370                 375                 380
Arg Tyr Tyr Pro Leu Gln Ala Thr Thr Leu Leu Ile Gln Pro Met Glu
385                 390                 395                 400
Ala Thr Ala Ala Ser
                405

<210> SEQ ID NO 6
<211> LENGTH: 1218
<212> TYPE: DNA
<213> ORGANISM: Rattus norvegicus

<400> SEQUENCE: 6
atgcgctgcg ctccgaccgc aggcgctgct ctagtgctat gcgcagctac tgcggggctg      60
ctgagcgcgc aagggcgccc tgcacagccg agccgccgc gcttcgcatc ctgggatgaa      120
atgaacttgc tggctcacgg gctgctgcag ctcggtcacg ggctgcggga cacgtggag       180
cgcacccgtg acagctgggc gcgctggaa cgccgcatgg ctgcctgcgg taacgcttgt      240
caggggccca aggggacaga cccgaaggat agagtccccg aaggccaggc tcctgagact      300
ctgcagagtt tacagactca actcaaggct cagaacagca gatccagca actgttccag       360
aaggtagccc agcagcagag atacctatca aagcagaatc tgagaataca gaatcttcag      420
agccagattg acctcttgac ccccacacac ctagacaatg gggtagacaa gacttcgagg      480
ggaaagaggc ttcccaagat ggcccagctc attggcttga ctcccaacgc cacccgctta      540
cacaggcctc cccgggactg ccaggaactc tttcaagaag gggagcggca cagtggactt      600
ttccagatcc agcctctggg atctccacca ttttttggtca actgtgagat gacttcagat      660
ggaggctgga cggtgattca gagacgcctg aacggctctg tggacttcaa tcagtcttgg      720
gaagcctaca agatggcttc ggagatccc aaggcgagt tctggctggg cctagagaag      780
atgcacagca tcacagggga ccgaggaagc cagttggctg tgcagctcca ggactggat      840
ggcaatgcca aattgctcca atttcctatc catttggggg gtgaggacac agcctacagc      900
ctgcagctca ccgagcccac ggccaatgag ctgggtgcca ccaatgtttc ccccaatggc      960
ctttccctgc ccttctctac ctgggaccaa gaccacgacc tccagggga ccttaactgt     1020
gccaagagcc tctctggtgg ctggtggttt ggcacctgca gccattccaa tctaaatgga     1080
caatacttcc actctattcc acggcaacgg cagcagcgta aaaagggat cttctggaaa     1140
acatggaagg gccgctacta tccactacag gctaccaccc tgttgatcca gcccatggag     1200
gctacagcag cctcttag                                                   1218

<210> SEQ ID NO 7
<211> LENGTH: 410
```

<212> TYPE: PRT
<213> ORGANISM: Mus musculus

<400> SEQUENCE: 7

```
Met Arg Cys Ala Pro Thr Ala Gly Ala Ala Leu Val Leu Cys Ala Ala
1               5                   10                  15

Thr Ala Gly Leu Leu Ser Ala Gln Gly Arg Pro Ala Gln Pro Glu Pro
            20                  25                  30

Pro Arg Phe Ala Ser Trp Asp Glu Met Asn Leu Leu Ala His Gly Leu
        35                  40                  45

Leu Gln Leu Gly His Gly Leu Arg Glu His Val Glu Arg Thr Arg Gly
    50                  55                  60

Gln Leu Gly Ala Leu Glu Arg Arg Met Ala Ala Cys Gly Asn Ala Cys
65                  70                  75                  80

Gln Gly Pro Lys Gly Lys Asp Ala Pro Phe Lys Asp Ser Glu Asp Arg
                85                  90                  95

Val Pro Glu Gly Gln Thr Pro Glu Thr Leu Gln Ser Leu Gln Thr Gln
            100                 105                 110

Leu Lys Ala Gln Asn Ser Lys Ile Gln Gln Leu Phe Gln Lys Val Ala
        115                 120                 125

Gln Gln Gln Arg Tyr Leu Ser Lys Gln Asn Leu Arg Ile Gln Asn Leu
    130                 135                 140

Gln Ser Gln Ile Asp Leu Leu Ala Pro Thr His Leu Asp Asn Gly Val
145                 150                 155                 160

Asp Lys Thr Ser Arg Gly Lys Arg Leu Pro Lys Met Thr Gln Leu Ile
                165                 170                 175

Gly Leu Thr Pro Asn Ala Thr His Leu His Arg Pro Pro Arg Asp Cys
            180                 185                 190

Gln Glu Leu Phe Gln Glu Gly Glu Arg His Ser Gly Leu Phe Gln Ile
        195                 200                 205

Gln Pro Leu Gly Ser Pro Pro Phe Leu Val Asn Cys Glu Met Thr Ser
    210                 215                 220

Asp Gly Gly Trp Thr Val Ile Gln Arg Arg Leu Asn Gly Ser Val Asp
225                 230                 235                 240

Phe Asn Gln Ser Trp Glu Ala Tyr Lys Asp Gly Phe Gly Asp Pro Gln
                245                 250                 255

Gly Glu Phe Trp Leu Gly Leu Glu Lys Met His Ser Ile Thr Gly Asn
            260                 265                 270

Arg Gly Ser Gln Leu Ala Val Gln Leu Gln Asp Trp Asp Gly Asn Ala
        275                 280                 285

Lys Leu Leu Gln Phe Pro Ile His Leu Gly Gly Glu Asp Thr Ala Tyr
    290                 295                 300

Ser Leu Gln Leu Thr Glu Pro Thr Ala Asn Glu Leu Gly Ala Thr Asn
305                 310                 315                 320

Val Ser Pro Asn Gly Leu Ser Leu Pro Phe Ser Thr Trp Asp Gln Asp
                325                 330                 335

His Asp Leu Arg Gly Asp Leu Asn Cys Ala Lys Ser Leu Ser Gly Gly
            340                 345                 350

Trp Trp Phe Gly Thr Cys Ser His Ser Asn Leu Asn Gly Gln Tyr Phe
        355                 360                 365

His Ser Ile Pro Arg Gln Arg Gln Glu Arg Lys Lys Gly Ile Phe Trp
    370                 375                 380

Lys Thr Trp Lys Gly Arg Tyr Tyr Pro Leu Gln Ala Thr Thr Leu Leu
385                 390                 395                 400
```

Ile Gln Pro Met Glu Ala Thr Ala Ala Ser
            405                 410

<210> SEQ ID NO 8
<211> LENGTH: 1869
<212> TYPE: DNA
<213> ORGANISM: Mus musculus

<400> SEQUENCE: 8

| | | |
|---|---|---:|
| acgggctcca gatcttcttc tgcaccagag caagtctaag tctgagccgg ctcccccaga | | 60 |
| actccagctg ctgggtcttg aactcctgcg ttccggagtc ctagcgttgc tgcacccaag | | 120 |
| gccaccccca gaatcatgcg ctgcgctccg acagcaggcg ctgccctggt gctatgcgcg | | 180 |
| gctactgcgg ggcttttgag cgcgcaaggg cgccctgcac agccagagcc accgcgcttt | | 240 |
| gcatcctggg acgagatgaa cttgctggct cacgggctgc tacagctcgg ccatgggctg | | 300 |
| cgcgaacacg tggagcgcac ccgtgggcag ctgggcgcgc tggagcgccg catggctgcc | | 360 |
| tgtggtaacg cttgtcaggg gcccaaggga aaagatgcac ccttcaaaga ctccgaggat | | 420 |
| agagtccctg aaggccagac tcctgagact ctgcagagtt tgcagactca gctcaaggct | | 480 |
| caaaacagca agatccagca attgttccag aaggtggccc agcagcagag atacctatca | | 540 |
| aagcagaatc tgagaataca gaatcttcag agccagatag acctcttggc ccccacgcac | | 600 |
| ctagacaatg gagtagacaa gacttcgagg ggaaagaggc ttcccaagat gacccagctc | | 660 |
| attggcttga ctcccaacgc cacccactta cacaggccgc cccgggactg ccaggaactc | | 720 |
| ttccaagaag gggagaggca cagtggactt ttccagatcc agcctctggg gtctccacca | | 780 |
| tttttggtca actgtgagat gacttcagat ggaggctgga cagtgattca gagacgcctg | | 840 |
| aacggctctg tggacttcaa ccagtcctgg gaagcctaca aggatggctt cggagatccc | | 900 |
| caaggcgagt ctggctgggc ctggaaaag atgcacagca tcacagggaa ccgaggaagc | | 960 |
| caattggctg tgcagctcca ggactgggat ggcaatgcca aattgctcca atttcccatc | | 1020 |
| catttggggg gtgaggacac agcctacagc ctgcagctca ctgagcccac ggccaatgag | | 1080 |
| ctgggtgcca ccaatgtttc ccccaatggc ctttccctgc ccttctctac ttgggaccaa | | 1140 |
| gaccatgacc tccgtgggga ccttaactgt gccaagagcc tctctggtgg ctggtggttt | | 1200 |
| ggtacctgta gccattccaa tctcaatgga caatacttcc actctatccc acggcaacgg | | 1260 |
| caggagcgta aaagggtat cttctggaaa acatggaagg gccgctacta tcctctgcag | | 1320 |
| gctaccaccc tgctgatcca gcccatggag gctacagcag cctcttagcc tcctcactgg | | 1380 |
| agcctggttc caggcctaag aagacagtga ctttggttgt ggccctgaga tttggccatt | | 1440 |
| ctctgctggg ggcaggagct ctaagtaggg ctatctgcgt cttgtggaca agaagaagc | | 1500 |
| ccgtaactgg agagactgga ggaccccttt tccgtgttgg ggtctgcaag cattgttgtc | | 1560 |
| tgaaacagtc agagcaacag gaaacaaatg gcccagatcc agaaaacatg ggctcgaggg | | 1620 |
| gcactgaata tcacttctcg cctaccagag aagttgggga tgcagaggga ccactacagt | | 1680 |
| ccaactagct gggcccttaa tggcggactc agtcatattg actgactgga gacagggtgc | | 1740 |
| caggagccct ggatacactc atggtgctgt tgtaggtgct gtggatgcac aggtgctaac | | 1800 |
| tgtggttccc aggcacaact cacagcattc ttacaataaa acaacctca gaacaaaaaa | | 1860 |
| aaaaaaaaa | | 1869 |

<210> SEQ ID NO 9
<211> LENGTH: 22

<212> TYPE: DNA
<213> ORGANISM: Homo sapiens

<400> SEQUENCE: 9
tctgggatct ccaccatttt tg                                          22

<210> SEQ ID NO 10
<211> LENGTH: 18
<212> TYPE: DNA
<213> ORGANISM: Homo sapiens

<400> SEQUENCE: 10
tcaccgtcca gcctccat                                               18

<210> SEQ ID NO 11
<211> LENGTH: 18
<212> TYPE: DNA
<213> ORGANISM: Homo sapiens

<400> SEQUENCE: 11
caactgtgag atgacttc                                               18

<210> SEQ ID NO 12
<211> LENGTH: 17
<212> TYPE: DNA
<213> ORGANISM: Homo sapiens

<400> SEQUENCE: 12
cgccacccgc ttacaca                                                17

<210> SEQ ID NO 13
<211> LENGTH: 22
<212> TYPE: DNA
<213> ORGANISM: Homo sapiens

<400> SEQUENCE: 13
cagaggctgg atctggaaaa gt                                          22

<210> SEQ ID NO 14
<211> LENGTH: 15
<212> TYPE: DNA
<213> ORGANISM: Homo sapiens

<400> SEQUENCE: 14
tgccaggaac tcttt                                                  15

<210> SEQ ID NO 15
<211> LENGTH: 23
<212> TYPE: DNA
<213> ORGANISM: Homo sapiens

<400> SEQUENCE: 15
tacaggctac caccctgttg atc                                         23

<210> SEQ ID NO 16
<211> LENGTH: 17
<212> TYPE: DNA
<213> ORGANISM: Homo sapiens

<400> SEQUENCE: 16
aaccgcgggc cctctag                                                17

<210> SEQ ID NO 17

```
<211> LENGTH: 17
<212> TYPE: DNA
<213> ORGANISM: Homo sapiens

<400> SEQUENCE: 17
ccatggaggc tacagca                                                  17

<210> SEQ ID NO 18
<211> LENGTH: 27
<212> TYPE: DNA
<213> ORGANISM: Homo sapiens

<400> SEQUENCE: 18
cttgaaggga ttgaaaagat aattagc                                       27

<210> SEQ ID NO 19
<211> LENGTH: 24
<212> TYPE: DNA
<213> ORGANISM: Homo sapiens

<400> SEQUENCE: 19
ccatgagtca gaaaagcatt gaac                                          24

<210> SEQ ID NO 20
<211> LENGTH: 17
<212> TYPE: DNA
<213> ORGANISM: Homo sapiens

<400> SEQUENCE: 20
aggtgagcat tttcctg                                                  17
```